United States Patent
Ju

(10) Patent No.: US 7,622,279 B2
(45) Date of Patent: Nov. 24, 2009

(54) PHOTOCLEAVABLE FLUORESCENT NUCLEOTIDES FOR DNA SEQUENCING ON CHIP CONSTRUCTED BY SITE-SPECIFIC COUPLING CHEMISTRY

(75) Inventor: Jingyue Ju, Englewood Cliffs, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 10/591,520

(22) PCT Filed: Mar. 3, 2005

(86) PCT No.: PCT/US2005/006960

§ 371 (c)(1),
(2), (4) Date: Jun. 4, 2007

(87) PCT Pub. No.: WO00/53805

PCT Pub. Date: Sep. 14, 2000

(65) Prior Publication Data

US 2007/0275387 A1    Nov. 29, 2007

Related U.S. Application Data

(60) Provisional application No. 60/550,007, filed on Mar. 3, 2004.

(51) Int. Cl.
*C12P 19/34* (2006.01)
*C12Q 1/68* (2006.01)
*C07G 3/00* (2006.01)
*C07H 19/04* (2006.01)
*C07H 21/00* (2006.01)
*C07H 21/02* (2006.01)

(52) U.S. Cl. .................. 435/91.1; 435/6; 435/91.2; 536/4.1; 536/23.1; 536/24.3; 536/25.3; 535/26.6

(58) Field of Classification Search .................. 435/6, 435/91.1, 91.2; 536/4.1, 23.1, 24.3, 25.3, 536/26.6
See application file for complete search history.

(56) References Cited

U.S. PATENT DOCUMENTS 4,711,955 A    12/1987    Ward et al.

(Continued)

FOREIGN PATENT DOCUMENTS

EP    0992511    4/2000

(Continued)

OTHER PUBLICATIONS

Axelrod, V. D. et al. (1978) Specific termination of RNA polymerase synthesis as a method of RNA and DNA sequencing. Nucleic Acids Res. 5(10):3549-3563.

(Continued)

*Primary Examiner*—Jezia Riley
(74) *Attorney, Agent, or Firm*—John P. White; Cooper & Dunham LLP

(57) ABSTRACT

This invention provides a method for determining the sequence of a DNA or an RNA, wherein (i) about 1000 or fewer copies of the DNA or RNA are bound to a solid substrate via 1,3-dipolar azide-alkyne cycloaddition chemistry and (ii) each copy of the DNA or RNA comprises a self-priming moiety.

21 Claims, 7 Drawing Sheets

U.S. PATENT DOCUMENTS

| | | | |
|---|---|---|---|
| 4,824,775 A | 4/1989 | Dattagupta | |
| 5,118,605 A | 6/1992 | Urdea | |
| 5,174,962 A | 12/1992 | Brennan | |
| 5,302,509 A | 4/1994 | Cheeseman | |
| 5,599,675 A | 2/1997 | Brenner | |
| 5,654,419 A | 8/1997 | Mathies | |
| 5,728,528 A | 3/1998 | Mathies | |
| 5,763,594 A | 6/1998 | Hiatt | |
| 5,770,367 A | 6/1998 | Southern | |
| 5,789,167 A | 8/1998 | Konrad | |
| 5,804,386 A | 9/1998 | Ju | |
| 5,808,045 A | 9/1998 | Hiatt | |
| 5,814,454 A | 9/1998 | Ju | |
| 5,834,203 A | 11/1998 | Katzir et al. | |
| 5,849,542 A | 12/1998 | Reeve et al. | |
| 5,853,992 A | 12/1998 | Glazer | |
| 5,869,255 A | 2/1999 | Mathies | |
| 5,872,244 A | 2/1999 | Hiatt | |
| 5,876,936 A | 3/1999 | Ju | |
| 5,885,775 A | 3/1999 | Haff et al. | |
| 5,945,283 A | 8/1999 | Kwok | |
| 5,952,180 A | 9/1999 | Ju | |
| 6,028,190 A | 2/2000 | Mathies | |
| 6,046,005 A | 4/2000 | Ju | |
| 6,074,823 A | 6/2000 | Koester | |
| 6,087,095 A | 7/2000 | Rosenthal et al. | |
| 6,136,543 A | 10/2000 | Anazawa et al. | |
| 6,197,557 B1 | 3/2001 | Markarov et al. | |
| 6,210,891 B1 | 4/2001 | Nyren et al. | |
| 6,214,987 B1 | 4/2001 | Hiatt | |
| 6,218,118 B1 | 4/2001 | Sampson | |
| 6,232,465 B1 | 5/2001 | Hiatt | |
| 6,312,893 B1 | 11/2001 | Van Ness et al. | |
| 6,316,230 B1 | 11/2001 | Egholm | |
| 6,361,940 B1 | 3/2002 | Van Ness et al. | |
| 6,613,508 B1 | 9/2003 | Ness et al. | |
| 6,613,513 B1 | 9/2003 | Parce et al. | |
| 6,627,748 B1 | 9/2003 | Ju et al. | |
| 6,632,655 B1 | 10/2003 | Mehta et al. | |
| 6,664,079 B2 * | 12/2003 | Ju et al. | 435/91.1 |
| 6,664,399 B1 | 12/2003 | Sabasan | |
| 6,787,308 B2 | 9/2004 | Balasubramanian et al. | |
| 6,833,246 B2 | 12/2004 | Balasubramanian | |
| 7,057,026 B2 | 6/2006 | Barnes et al. | |
| 7,057,031 B2 | 6/2006 | Olejnik et al. | |
| 7,074,597 B2 | 7/2006 | Ju | |
| 7,078,499 B2 | 7/2006 | Odedra et al. | |
| 2002/0012966 A1 | 1/2002 | Shi et al. | |
| 2002/0168642 A1 | 11/2002 | Drukier | |
| 2003/0008285 A1 | 1/2003 | Fischer | |
| 2003/0022225 A1 | 1/2003 | Montforte et al. | |
| 2003/0027140 A1 | 2/2003 | Ju et al. | |
| 2003/0044871 A1 | 3/2003 | Cutsforth et al. | |
| 2003/0054360 A1 | 3/2003 | Gold et al. | |
| 2003/0099972 A1 | 5/2003 | Olejnik et al. | |
| 2003/0166282 A1 | 9/2003 | Brown et al. | |
| 2003/0190680 A1 | 10/2003 | Rothschild et al. | |
| 2003/0198982 A1 | 10/2003 | Seela et al. | |
| 2004/0185466 A1 | 9/2004 | Ju et al. | |
| 2005/0032081 A1 | 2/2005 | Ju et al. | |
| 2005/0170367 A1 | 8/2005 | Quake | |
| 2005/0239134 A1 | 10/2005 | Gorenstein et al. | |
| 2006/0003352 A1 | 1/2006 | Lipkin et al. | |
| 2006/0057565 A1 | 3/2006 | Ju et al. | |
| 2006/0105461 A1 | 5/2006 | Tom-Moy et al. | |
| 2006/0160081 A1 | 7/2006 | Milton | |
| 2006/0240439 A1 | 10/2006 | Smith et al. | |
| 2006/0252923 A1 * | 11/2006 | Olejnik et al. | 536/25.32 |
| 2006/0252938 A1 | 11/2006 | Sava et al. | |
| 2007/0166705 A1 | 7/2007 | Milton | |
| 2007/0275387 A1 | 11/2007 | Ju et al. | |

FOREIGN PATENT DOCUMENTS

| | | |
|---|---|---|
| WO | WO 91/06678 | 5/1991 |
| WO | WO/92/10587 | 6/1992 |
| WO | WO 00/53805 | 9/2000 |
| WO | WO 01/27625 | 4/2001 |
| WO | WO 01/92284 | 12/2001 |
| WO | WO 02/22883 | 3/2002 |
| WO | WO 02/29003 | 4/2002 |
| WO | WO 02/079519 | 10/2002 |
| WO | WO 2004/007773 | 1/2004 |
| WO | WO 2004/055160 | 1/2004 |
| WO | WO 2004/018493 | 3/2004 |
| WO | WO 2004/018497 | 3/2004 |
| WO | WO/2004/018497 | 4/2004 |
| WO | WO 2005/084367 | 9/2005 |
| WO | WO 2006/073436 | 7/2006 |
| WO | WO 2007/002204 | 1/2007 |
| WO | WO/2007/053702 | 5/2007 |
| WO | WO/2007/053719 | 5/2007 |
| WO | WO/2007/062105 | 5/2007 |
| WO | WO/2008/069973 | 6/2008 |

OTHER PUBLICATIONS

Badman, E. R. et al. (2000) A Parallel Miniature Cylindrical Ion Trap Array. *Anal. Chem.* 72:3291-3297.

Badman, E. R. et al. (2000) Cylindrical Ion Trap Array with Mass Selection by Variation in Trap Dimensions. *Anal. Chem.* 72:5079-5086.

Benson, S. C., Mathies, R. A. and Glazer, A. N. (1993) Heterodimeric DNA-binding dyes designed for energy transfer: stability and applications of the DNA complexes. *Nucleic Acids Res.* 21:5720-5726.

Benson, S. C., Singh, P. and Glazer, A. N. (1993) Heterodimeric DNA-binding dyes designed for energy transfer: synthesis and spectroscopic properties. *Nucleic Acids Res.* 21:5727-5735.

Burgess, K. et al. (1997) Photolytic Mass Laddering for Fast Characterization of Oligomers on Single Resin Beads. *J. Org. Chem.* 62:5662-5663.

Canard, B. et al. (1995) Catalytic editing properties of DNA polymerases. *Proc. Natl. Acad. Sci. USA* 92:10859-10863.

Caruthers, M. H. (1985) Gene synthesis machines: DNA chemistry and its uses. *Science* 230:281-285.

Chee, M. et al. (1996) Accessing genetic information with high-density DNA arrays. *Science* 274:610-614.

Chen, X. and Kwok, P.-Y. (1997) Template-directed dye-terminator incorporation (TDI) assay: a homogeneous DNA diagnostic method based on fluorescence resonance energy transfer. *Nucleic Acids Res.* 25:347-353.

Edwards, J. et al. (2001) DNA sequencing using biotinylated dideoxynucleotides and mass spectrometry. *Nucleic Acids Res.* 29(21):e104.

Griffin, T. J. et al. (1999) Direct Genetic Analysis by Matrix-Assisted Laser Desorption/Ionization Mass Spectrometry. *Proc. Nat. Acad. Sci. USA* 96:6301-6306.

Hacia, J. G., Edgemon, K., Sun, B., Stern, D., Fodor, S. A., and Collins, F.S. (1998) Two Color Hybridization Analysis Using High Density Oligonucleotide Arrays and Energy Transfer Dyes. *Nucleic Acids Res.* 26:3865-6.

Hyman, E. D. (1988) A new method of sequencing DNA. *Analytical Biochemistry* 174:423-436.

Ireland R. E. and Varney M. D. (1986) Approach to the total synthesis of chlorothricolide—synthesis of (+/−)-19.20-dihydro-24-O-methylchlorothricolide, methyl-ester,ethyl carbonate. *J. Org. Chem.* 51:635-648.

Jiang-Baucom, P. et al. (1997) DNA Typing of Human Leukocyte Antigen Sequence Polymorphisms by Peptide Nucleic Acid Probes and MALDI-TOF Mass Spectrometry. *Anal. Chem.* 69:4894-4896.

Ju, J., Glazer, A. N. and Mathies, R. A. (1996) Energy transfer primers: A new fluorescence labeling paradigm for DNA sequencing and analysis. *Nature Medicine* 2:246-249.

Ju, J., Ruan, C., Fuller, C. W., Glazer, A. N. and Mathies, R. A. (1995) Fluorescence energy transfer dye-labeled primers for DNA sequencing and analysis. *Proc. Natl. Acad. Sci. USA* 92:4347-4351.

Kamal, A., Laxman, E., and Rao, N. V. (1999) A mild and rapid regeneration of alcohols from their allylic ethers by chlorotrimethylsilane/sodium iodide. *Tetrahedron Lett.* 40:371-372.

Lee, L. G. et al. (1992) DNA sequencing with dye-labeled terminators and T7 DNA polymerase: effect of dyes and dNTPs on incorporation of dye terminators and probability analysis of termination fragments. *Nucleic Acids Res.* 20:2471-2483.

Lee, L. G. et al. (1997) New energy transfer dyes for DNA Sequencing. *Nucleic Acids Res.* 25:2816-2822.

Li, J. (1999) Single Oligonucleotide Polymorphism Determination Using Primer Extension and Time-of-Flight Mass Spectrometry. *Electrophoresis*, 20:1258-1265.

Liu, H. et al. (2000) Development of Multichannel Devices with an Array of Electrospray Tips for High-Throughput Mass Spectrometry. *Anal. Chem.* 72:3303-3310.

Lyamichev, A. et al. (1999) Polymorphism Identification and Quantitative Detection of Genomic DNA by Invasive Cleavage of Oligonucleotide Probes. *Nat. Biotech.* 17:292-296.

Metzker, M. L., et al. (1994) Termination of DNA synthesis by novel 3'-modified deoxyribonucleoside 5'-triphosphates. Nucleic Acids Res. 22:4259-4267.

Olejnik, J., et al. (1995) Photocleavable biotin derivatives: a versatile approach for the isolation of biomolecules. *Proc. Natl. Acad. Sci. USA.* 92:7590-7594.

Pelletier, H., Sawaya, M. R., Kumar, A., Wilson, S. H., and Kraut J. (1994) Structures of ternary complexes of rat DNA polymerase β, a DNA template-primer, and ddCTP. *Science* 264:1891-1903.

Prober, J. M., Trainor, G. L., Dam, R. J., Hobbs, F. W., Robertson, C. W., Zagursky, R. J., Cocuzza, A. J., Jensen, M. A., Baumeister K. (1987) A system for rapid DNA sequencing with fluorescent chain-terminating dideoxynucleotides. *Science* 238:336-341.

Ronaghi, M., Uhlen, M., and Nyren, P. (1998) A sequencing Method based on real-time pyrophosphate. *Science* 281:364-365.

Rosenblum, B. B. et al. (1997) New dye-labeled terminators for improved DNA sequencing patterns. *Nucleic Acids Res.* 25:4500-4504.

Ross, P. et al. (1998) High Level Multiplex Genotyping by MALDI-TOF Mass Spectrometry. *Nat. Biotech.* 16:1347-1351.

Ross, P. L. et al. (1997) Discrimination of Single-Nucleotide Polymorphisms in Human DNA Using Peptide Nucleic Acid Probes Detected by MALDI-TOF Mass Spectrometry. *Anal. Chem.* 69:4197-4202.

Saxon, E. and Bertozzi, C. R. (2000) Cell surface engineering by a modified Staudinger reaction. *Science* 287:2007-2010.

Schena, M., Shalon, D., Davis, R., and Brown, P. O. (1995) Quantitative monitoring of gene expression patterns with a complementary DNA microarray. *Science* 270:467-470.

Speicher, M. R., Ballard, S. G. and Ward, D. C., (1996) "Karyotyping human chromosomes by combinatorial multi-fluor FISH". *Nature Genetics* 12:368-375.

Stoerker, J. et al. (2000) Rapid Genotyping by MALDI-monitored nuclease selection from probe libraries. *Nat. Biotech.* 18:1213-1216.

Welch, M. B., and Burgess, K. (1999) Synthesis of fluorescent, photolabile 3'-O-protected nucleoside triphosphates for the base addition sequencing scheme. *Nucleosides and Nucleotides* 18:197-201.

Woolley, A. T. et al. (1997) High-Speed DNA Genotyping Using Microfabricated Capillary Array Electrophoresis Chips. *Anal. Chem.* 69:2181-2186.

Fei, Z. et al. (1998) MALDI-TOF mass spectrometric typing of single nucleotide polymorphisms with mass-tagged ddNTPs. *Nucleic Acids Research* 26(11):2827-2828.

Olejnik, J. et al. (1999) Photocleavable peptide-DNA conjugates: synthesis and applications to DNA analysis using MALDI-MS. *Nucleic Acids Res.* 27(23):4626-4631.

Arbo, et al. (1993) Solid Phase Synthesis of Protected Peptides Using New Cobalt (III) Amine Linkers, *Int. J. Peptide Protein Res.* 42:138-154.

Chiu, N.H., Tang, K., Yip, P., Braun, A., Koster, H., and Cantor C. R. (2000) Mass spectrometry of single-stranded restriction fragments captured by an undigested complementary sequence. *Nucleic Acids Res.* 28:E31.

Fu, D. J., Tang, K., Braun, A., Reuter, D. Darnhofer-Demar, B.,Little D. P., O'Donnell, M. J., Cantor, C.R., and Koster, (1998) Sequencing exons 5 to 8 of the p53 gene by MALDI-TOF mass spectrometry. *Nat. Biotechnol.* 16:381-384.

Monforte, J. A., and Becker, C. H. (1997) High-throughput DNA analysis by time-of-flight mass spectrometry. *Nat. Med.* 3(3):360-362.

Roskey, M. T, Juhasz P., Smirnov, I. P., Takach, E.J.,and Martin, S.A. (1996) Haff L.A., DNA sequencing by delayed extraction-matrix-assisted laser desorption/ionization time of flight mass spectrometry. *Proc. Natl. Acad. Sci. USA.* 93:4724-4729.

Tang, K., Fu, D. J., Julien, D., Braun, A., Cantor, C. R. and Koster H. (1999) Chip-based genotyping by mass spectrometry. *Proc. Natl. Acad. Sci. USA.* 96:10016-10020.

Tong, X. and Smith L. M. (1992) Solid-Phase Method for the Purification of DNA Sequencing Reactions. Anal. Chem. 64:2672-2677.

Jurinke, C., van de Boom, D., Collazo, V., Luchow, A., Jacob, A, Koster, H., (1997) Recovery of nucleic acids from immobilized biotin-streptavidin complexes using ammonium hydroxide and application in MALDI-TOF mass spectrometry. *Anal. Chem.* 69:904-910.

Jingyue Ju, et al., (1996) "Cassette labeling for facile construction of energy transfer fluorescent primers", Nuc. Acids Res. 24(6):1144-1148.

Bergseid M., Baytan A.R., Wiley J.P., Ankener W.M., Stolowitz, Hughs K.A., Chestnut J.D., (2000) "Small-molecule base chemical affinity system for the purification of proteins", BioTechniques 29:1126-1133.

Hultman et al., (1989) "Direct Solid Phase Sequencing of Genomic and Plasmid DNA Using Magnetic Beads as Solid Support", *Nucleic Acids Research*, 17(3):4937-4946.

Buschmann et al., (1999) "The Complex Formation of α,ω-Dicarboxylic Acids and α,ω-Diols with Cucurbituril and α-Cyclodextrin", Acta Chim. Slov. 46(3):405-411.

Kolb et al., (2001) "Click Chemistry: Diverse Chemical Function From a Few Good Reactions", Angew. Chem. Int. Ed. 40:2004-2021.

Lewis et al., (2002) "Click Chemistry in Situ: Acetylcholinesterase as a Reaction Vessel for the Selective Assembly of a Femtomolar Inhibitor from an Array of Building Blocks", Angew. Chem. Int. Ed., 41(6):1053-1057.

Seo et al., (2003) "Click Chemistry to Construct Fluorescent Oligonucleotides for DNA Sequencing", J. Org. Chem. 68:609-612.

Fallahpour, (2000) "Photochemical and Thermal reactions of Azido-Oligopyridines: Diazepinones, a New Class of Metal-Complex Ligands", Helvetica Chimica Acta. 83:384-393.

Ikeda, K. et al., (1995) "A Non-Radioactive DNA Sequencing Method Using Biotinylated Dideoxynucleoside Triphosphates and Delta TTH DNA Polymerase" DNA Research, 2(31):225-227.

Kim Sobin et al., (2002) "Solid Phase Capturable Dideoxynucleotides for Multiplex Genotyping Using Mass Spectrometry" Nucleic Acids Research, 30(16):e85.1-e85.6.

Wendy S Jen, John J.M. Wiener, and David W.C. MacMillan, (2000) "New Strategies for Organic Catalysis: The First Enantioselective Orgacnocatalytic 1,3-Dipolar Cycloaddition" J. Am. Chem. Soc., 122, 9874-9875.

Supplementary European Search Report issued Feb. 16, 2004 in connection with European Patent Application No. 01 97 7533.

Supplementary European Search Report issued Feb. 9, 2007 in connection with European Patent Application No. 03 76 4568.6.

Supplementary European Search Report issued May 25, 2005 in connection with European Patent Application No. 02 72 8606.1.

Supplementary European Search Report issued Jun. 7, 2005 in connection with European Patent Application No. 01 96 8905.

International Preliminary Examination Report issued on Mar. 18, 2005 in connection with PCT/US03/21818.

International Preliminary Examination Report issued on Apr. 3, 2003 in connection with PCT/US01/31243.

International Preliminary Examination Report issued on Feb. 25, 2003 in connection with PCT/US01/28967.

International Preliminary Examination Report issued on Mar. 17, 2003 in connection with PCT/US02/09752.
International Preliminary Report on Patentability issued on Sep. 5, 2006 in connection with PCT/US05/006960.
International Search Report issued May 13, 2002 in connection with PCT/US01/31243.
International Search Report issued Jan. 23, 2002 in connection with PCT/US01/28967.
International Search Report issued Sep. 18, 2002 in connection with PCT/US02/09752.
International Search Report issued Sep. 26, 2003 in connection with PCT/US03/21818.
International Search Report issued Jun. 8, 2004 in connection with PCT/US03/39354.
International Search Report issued Nov. 4, 2005 in connection with PCT/US05/06960.
International Search Report issued Dec. 15, 2006 in connection with PCT/US05/13883.
Written Opinion of the International Searching Authority issued Oct. 27, 2005 in connection with PCT/US05/06960.
Written Opinion of the International Searching Authority issued Dec. 15, 2006 in connection with PCT/US05/13883.
Elango, N. et al. (1983) "Amino Acid Sequence of Human Respiratory Syncytial Virus Nucleocapsid Protein" Nucleic Acids Research, 11(17):5941-5951.
Buck, G.A. et al. (1999) "Design Strategies and Performance of Custom DNA Sequencing Primers", BioTechniques, 27(3):528-536.
Hafliger, D. et al. (1997) "Seminested RT-PCR Systems for Small Round Structured Viruses and Detection of Enteric Viruses in Seafood", International Journal of Food Microbiology, 37:27-36.
Leroy, E.M. et al. (2000) "Diagnosis of Ebola Haemorrhagic Fever by RT-PCR in an Epidemic Setting", Journal of Medical Virology, 60:463-467.
Kokoris, M. et al. (2000) "High-throughput SNP Genotyping With the Masscode System", Molecular Diagnosis, 5(4):329-340.
Kim, S. et al. (2003) "Multiplex Genotyping of the Human β2-adrenergic Receptor Gene Using Solid-phase Capturable Dideoxynucleotides and Mass Spectrometry", Analytical Biochemistry, 316:251-258.
Haff, L. A. et al. (1977) Multiplex Genotyping of PCR Products with Mass Tag-Labeled Primers. *Nucleic Acids Res.* 25(18):3749-3750.
Tuncel et al. (1999) Catalytically Self-Threading Polyrotaxanes, Chem. Comm. 1509-1510.
Notification of Transmittal of International Search Report and Written Opinion, issued Nov. 23, 2007.
Meng et al., (2006), Design and Synthesis of a Photocleavable Fluorescent Nucleotide 3'-O-Allyl-dGTP-PC-Biodipy-FL-510 as a Reversible Terminator for DNA Sequencing by Synthesis, J. Org. Chem 71:3248-3252.
Li et al., (2003), A photocleavable Fluorescent Nucleotide for DNA Sequencing and Analysis, PNAS, 100(2):414-419.
Seo et al., (2004), Photocleavable Fluorescent Nucleotides for DNA Sequencing on a Chip Constructed by Site-Specific Coupling Chemistry, PNAS 101(15):5488-5493.
Seo et al., (2004), Four-Color DNA Sequencing by Synthesis on a Chip Using Photocleavable Fluorescent Nucleotides, PNAS 102(17):5926-5931.
Ruparel et al., (2005), Design and Synthesis of a 3'-O-Allyl Photocleavable Fluorescent Nucleotide as a Reversible Terminator for DNA Sequencing by Synthesis, PNAS, 102(17):5932-5937.
International Search Report issued Oct. 29, 2007 in connection with PCT International Application No. PCT/US07/13559.
U.S. Appl. No. 11/894,808, filed Aug. 20, 2007.
U.S. Appl. No. 11/894,690, filed Aug. 20, 2007.
U.S. Appl. No. 11/810,509, filed Jun. 5, 2007.
U.S. Appl. No. 09/684,670, filed Oct. 6, 2000, Ju et al.
U.S. Appl. No. 12/085,343, filed May 19, 2008.
Official Action issued Mar. 14, 2008 in connection with European Patent Application No. 07004522.4.
Office Action issued Jun. 24, 2008 in connection with U.S. Appl. No. 11/894,690.
Office Action issued Jul. 8, 2008 in connection with U.S. Appl. No. 10/591,520.
Notification of Transmittal of International Search Report and Written Opinion, issued Feb. 6, 2008 in connection with International Application No. PCT/US06/42739.
Notification Concerning Transmittal of International Preliminary Report on Patentability (Including Written Opinion of the International Searching Authority) issued May 15, 2008 in connection with PCT/US2006/042698.
Notification of Transmittal the International Search Report and Written Opinion, issued May 22, 2008 in connection with International Application No. PCT/US06/45180.
Notification of Transmittal the International Search Report and Written Opinion, issued Aug. 16, 2008 in connection with International Application No. PCT/US07/24646.
Bai et al. (2003) "Photocleavage of a 2-nitrobenzyl linker bridging a fluorophore to the 5' end of DNA," PNAS, vol. 100, No. 2, pp. 409-413.
Nielsen et al. (2004) "Multiplexed sandwich assays in microarray format," Journal of Immunological Methods, vol. 290, pp. 107-120.
Zhang et al. (2002) "Synthesis of Releasable Electrophore Tags for Applications in Mass Spectrometry," Bioconjugate Chem, vol. 13, pp. 1002-1012.
Sep. 3, 2008 Office Action issued in connection with U.S. Appl. No. 11/894,808.
Nickel W, et al. (1992) "Interactions of azidothymidine triphosphate with the cellular DNA polymerases alpha, delta, and epsilon and with DNA primase". Journal of Biological Chemistry. 267(2):848-854.
Notification of Transmittal the International Search Report and Written Opinion, issued Sep. 9, 2008 in connection with International Application No. PCT/US06/24157.
Hanshaw et al. (2004) "An Indicator displacement system for fluorescent detection of phosphate oxyanions under physiological conditions" Tetrahedron Letters, vol. 45, pp. 8721-8724.
U.S. Appl. No. 12/084,338, filed Apr. 28, 2008.
Official Action issued Mar. 3, 2007 in connection with European Patent Application No. 07004522.4.
U.S. Appl. No.11/922,385, filed Dec. 14, 2007.
Supplementary European Search Report issued Oct. 9, 2008 in connection with PCT International Application No. 05724495.6.
Green, T.W. and Wuts, P.G.M. Protective Groups in Organic Synethesis. 3rd ed. New York: John Wiley & Sons, Inc., 1999. 96-99, 190-191, 260-261, 542-543 and 750-751.
Huang, B.G., Bobek, M. Synthesis and in vitro antitumor activity of some amino-deoxy 7-hexofuranosylpyrrolo[2,3-d]pyrimidines. Carbohydrate Research. 1998;308(3-4):319-28.
Azhayev, A. et al., 1-Alkylthioalkylation of Nucleoside Hydroxyl Functions and Its Synthetic Applications: A New Versatile Method in Nucleoside Chemistry. Tetrahedron Letters, 1991; 32(51), 7593-7596.
Loubinoux, B., Tabbache, S., Gerardin, P. and Miazimbakana, J. Protection Des Phenols Par Le Groupement Azidomethylene Application A La Synthese De Phenols Instables. Tetrahedron, 1988; 44(19): 6055-6064.
Notification Concerning Transmittal of International Preliminary Report on Patentability issued Dec. 24, 2008 in connection with International Application No. PCT/US07/13559.
Notification Concerning Transmittal of the International Search Report and the Written Opinion of the International Search Authority, or the Declaration issued Jan. 30, 2009 in connection with International Application No. PCT/US08/11913.
Notification Concerning Transmittal of the International Search Report and the Written Opinion of the International Searching Authority, or the Declaration issued Feb. 10, 2009 in connection with International Application No. PCT/US08/11891.
Ju J et al. Four-color DNA sequencing by synthesis using cleavable fluorescent nucleotide reversible terminators. Proc Natl Acad Sci U S A. Dec. 26, 2006; 103(52):19635-40. Epub Dec. 14, 2006.
Notification Concerning Transmittal of International Preliminary Report on Patentability issued Mar. 19, 2009 in connection with International Application No. PCT/US06/024157.
PCT International Application Publication No. WO 00/50642, published Aug. 31, 2000 to Caliper Technologies Corp.
PCT International Application Publication No. WO 00/50172, published Aug. 31, 2000 to Caliper Technologies Corp.

Notice of Allowance issued Feb. 24, 2009 in connection with U.S. Appl. No. 11/894,690.

Notice of Allowance issued Mar. 23, 2009 in connection with U.S. Appl. No. 11/894,808.

Notification Concerning Transmittal of International Preliminary Report on Pantentability issued Mar. 26, 2009 in connection with International Application No. PCT/US06/042739.

Extended European Search Report issued Jul. 18, 2007 in connection with European Patent Application No. 07004522.4.

Partial European Search Report issued Apr. 26, 2007 in connection with European Patent Application No. 07004522.4.

Kraevskii, A.A. et al., (1987), Substrate Inhibitors of DNA Biosynthesis, Molecular Biology, 21:25-29.

Henner, W.D. et al., (1983), Enzyme Action at 3' Termini of Ionizing Radiation-Induced DNA Strand Breaks, J. Biol. Chem. 258(24):15198-15205.

Office Action issued Oct. 25, 2002 in connection with U.S. Appl. No. 09/972,364.

Office Action issued Mar. 14, 2003 in connection with U.S. Appl. No. 09/972,364.

Office Action issued Aug. 10, 2007 in connection with U.S. Appl. No. 11/119,231.

Office Action issued Sep. 21, 2007 in connection with U.S. Appl. No. 10/380,256.

Notice of Allowance issued Sep. 6, 2007 in connection with U.S. Appl. No. 10/702,203.

Restriction Requirement issued in connection with U.S. Appl. No. 10/521,206, Oct. 1, 2007.

Office Action issued Nov. 14, 2007 in connection with U.S. Appl. No. 10/735,081.

Official Action issued May 21, 2007 in connection with European Patent Application No. 01968905.8.

Official Action issued Mar. 31, 2006 in connection with European Patent Application No. 01968905.8.

\* cited by examiner

PHOTOCLEAVABLE FLUORESCENT NUCLEOTIDES FOR DNA SEQUENCING ON CHIP CONSTRUCTED BY SITE-SPECIFIC COUPLING CHEMISTRY

This application is a §371 national stage of PCT International Application No. PCT/US2005/006960, filed Mar. 3, 2005, and claims the benefit of U.S. provisional application no. 60/550,007, filed Mar. 3, 2004, the contents of all of which are hereby incorporated by reference into this application.

The invention disclosed herein was made with Government support under Center of Excellence in Genomic Science grant No. P50 HG002806 from the National Institutes of Health, U.S. Department of Health and Human Services. Accordingly, the U.S. Government has certain rights in this invention.

Throughout this application, various publications are referenced in parentheses by number. Full citations for these references may be found at the end of each experimental section. The disclosures of these publications in their entireties are hereby incorporated by reference into this application to more fully describe the state of the art to which this invention pertains.

BACKGROUND

DNA sequencing is a fundamental tool for biological science. The completion of the Human Genome Project has set the stage for screening genetic mutations to identify disease genes on a genome-wide scale (1). Accurate high-throughput DNA sequencing methods are needed to explore the complete human genome sequence for applications in clinical medicine and health care. Recent studies have indicated that an important route for identifying functional elements in the human genome involves sequencing the genomes of many species representing a wide sampling of the evolutionary tree (2). To overcome the limitations of the current electrophoresis-based sequencing technology (3-5), a variety of new DNA-sequencing methods have been investigated. Such approaches include sequencing by hybridization (6), mass spectrometry based sequencing (7-9), and sequence-specific detection of single-stranded DNA using engineered nanopores (10). More recently, DNA sequencing by synthesis (SBS) approaches such as pyrosequencing (11), sequencing of single DNA molecules (12) and polymerase colonies (13) have been widely explored.

The concept of DNA sequencing by synthesis was revealed in 1988 (14). This approach involves detection of the identity of each nucleotide immediately after its incorporation into a growing strand of DNA in a polymerase reaction. Thus far, no complete success has been reported in using such a system to sequence DNA unambiguously. An SBS approach using photocleavable fluorescent nucleotide analogues on a surface was proposed in 2000 (15). In this approach, modified nucleotides are used as reversible terminators, in which a different fluorophore with a distinct fluorescent emission is linked to each of the 4 bases through a photocleavable linker and the 3'-OH group is capped by a small chemical moiety. DNA polymerase incorporates only a single nucleotide analogue complementary to the base on a DNA template covalently linked to a surface. After incorporation, the unique fluorescence emission is detected to identify the incorporated nucleotide and the fluorophore is subsequently removed photochemically. The 3'-OH group is then chemically regenerated, which allows the next cycle of the polymerase reaction to proceed. Since the large surface on a DNA chip can have a high density of different DNA templates spotted, each cycle can identify many bases in parallel, allowing the simultaneous sequencing of a large number of DNA molecules. The advantage of using photons as reagents for initiating photoreactions to cleave the fluorophore is that no additional chemical reagents are required to be introduced into the system and clean products can be generated with no need for subsequent purification.

SUMMARY

This invention provides a method for determining the sequence of a DNA, wherein (i) about 1000 or fewer copies of the DNA are bound to a solid substrate via 1,3-dipolar azide-alkyne cycloaddition chemistry and (ii) each copy of the DNA comprises a self-priming moiety, comprising performing the following steps for each nucleic acid residue of the DNA to be sequenced:

(a) contacting the bound DNA with DNA polymerase and four photocleavable fluorescent nucleotide analogues under conditions permitting the DNA polymerase to catalyze DNA synthesis, wherein (i) the nucleotide analogues consist of an analogue of G, an analogue of C, an analogue of T and an analogue of A, so that a nucleotide analogue complementary to the residue being sequenced is bound to the DNA by the DNA polymerase, and (ii) each of the four analogues has a pre-determined fluorescence wavelength which is different than the fluorescence wavelengths of the other three analogues;

(b) removing unbound nucleotide analogues; and (c) determining the identity of the bound nucleotide analogue, thereby determining the sequence of the DNA.

This invention also provides a method for determining the sequence of an RNA, wherein (i) about 1000 or fewer copies of the RNA are bound to a solid substrate via 1,3-dipolar azide-alkyne cycloaddition chemistry and (ii) each copy of the RNA comprises a self-priming moiety, comprising performing the following steps for each nucleic acid residue of the RNA to be sequenced:

(a) contacting the bound RNA with RNA polymerase and four photocleavable fluorescent nucleotide analogues under conditions permitting the RNA polymerase to catalyze RNA synthesis, wherein (i) the nucleotide analogues consist of an analogue of G, an analogue of C, an analogue of U and an analogue of A, so that a nucleotide analogue complementary to the residue being sequenced is bound to the RNA by the RNA polymerase, and (ii) each of the four analogues has a pre-determined fluorescence wavelength which is different than the fluorescence wavelengths of the other three analogues;

(b) removing unbound nucleotide analogues; and (c) determining the identity of the bound nucleotide analogue, thereby determining the sequence of the RNA.

This invention also provides a composition of matter comprising a solid substrate having a DNA bound thereto via 1,3-dipolar azide-alkyne cycloaddition chemistry, wherein (i) about 1000 or fewer copies of the DNA are bound to the solid substrate, and (ii) each copy of the DNA comprises a self-priming moiety.

This invention also provides a composition of matter comprising a solid substrate having an RNA bound thereto via 1,3-dipolar azide-alkyne cycloaddition chemistry, wherein (i) about 1000 or fewer copies of the RNA are bound to the solid substrate, and (ii) each copy of the RNA comprises a self-priming moiety.

DETAILED DESCRIPTION OF THE INVENTION

Terms

The following definitions are presented as an aid in understanding this invention:

| | |
|---|---|
| A | Adenine; |
| C | Cytosine; |
| DNA | Deoxyribonucleic acid; |
| G | Guanine; |
| RNA | Ribonucleic acid; |
| SBS | Sequencing by synthesis; |
| T | Thymine; and |
| U | Uracil. |

"Nucleic acid" shall mean any nucleic acid, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996 1997, Roche Molecular Systems, Inc., Branchburg, N.J., USA).

As used herein, "self-priming moiety" shall mean a nucleic acid moiety covalently bound to a nucleic acid to be transcribed, wherein the bound nucleic acid moiety, through its proximity with the transcription initiation site of the nucleic acid to be transcribed, permits transcription of the nucleic acid under nucleic acid polymerization-permitting conditions (e.g. the presence of a suitable polymerase, nucleotides and other reagents). That is, the self-priming moiety permits the same result (i.e. transcription) as does a non-bound primer. In one embodiment, the self-priming moiety is a single stranded nucleic acid having a hairpin structure. Examples of such self-priming moieties are shown in the Figures.

"Hybridize" shall mean the annealing of one single-stranded nucleic acid to another nucleic acid based on sequence complementarity. The propensity for hybridization between nucleic acids depends on the temperature and ionic strength of their milieu, the length of the nucleic acids and the degree of complementarity. The effect of these parameters on hybridization is well known in the art (see Sambrook J, Fritsch E F, Maniatis T. 1989. Molecular cloning: a laboratory manual. Cold Spring Harbor Laboratory Press, New York.)

Figure 6:
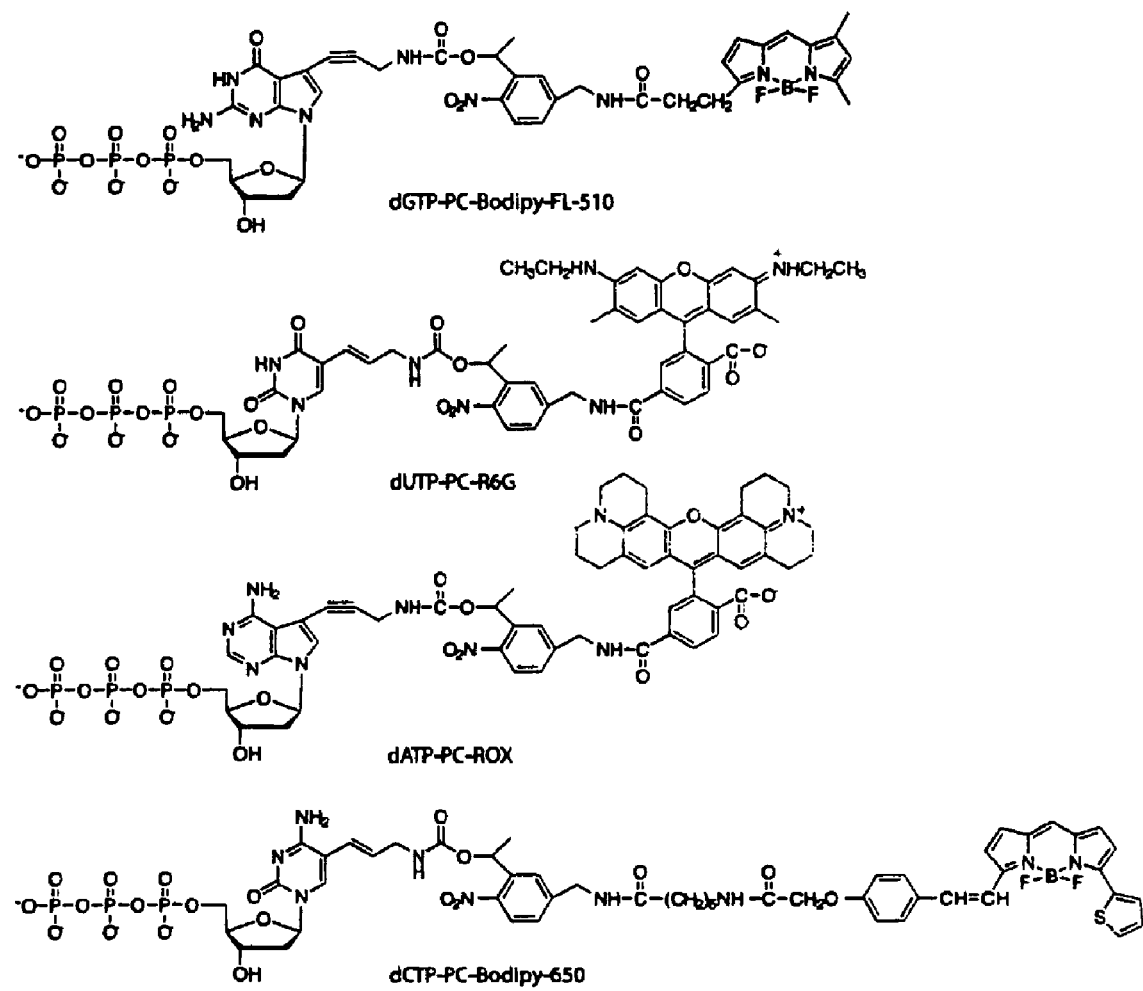
FIG. 6. Structures of dGTP-PC-Bodipy-FL-510 ($\lambda_{abs\ (max)}$=502 nm; $\lambda_{em\ (max)}$=510 nm), dUTP-PC-R6G ($\lambda_{abs\ (max)}$=525 nm; $\lambda_{em\ (max)}$=550 nm), dATP-PC-ROX ($\lambda_{abs\ (max)}$=575 nm; $\lambda_{em\ (max)}$=602 nm), and dCTP-PC-Bodipy-650 ($\lambda_{abs\ (max)}$=630 nm; $\lambda_{em\ (max)}$=650 nm)

As used herein, "nucleotide analogue" shall mean an analogue of A, G, C, T or U which is recognized by DNA or RNA polymerase (whichever is applicable) and incorporated into a strand of DNA or RNA (whichever is appropriate). Examples of nucleotide analogues include, without limitation 7-deaza-adenine, 7-deaza-guanine, the analogues of deoxynucleotides shown in FIG. 6, analogues in which a label is attached through a cleavable linker to the 5-position of cytosine or thymine or to the 7-position of deaza-adenine or deaza-guanine, analogues in which a small chemical moiety such as —CH₂OCH₃ or —CH₂CH=CH₂ is used to cap the —OH group at the 3'-position of deoxyribose, and analogues of related dideoxynucleotides. Nucleotide analogues, including dideoxynucleotide analogues, and DNA polymerase-based DNA sequencing are also described in U.S. Pat. No. 6,664,079.

Embodiments of the Invention

This invention provides a method for determining the sequence of a DNA, wherein (i) about 1000 or fewer copies of the DNA are bound to a solid substrate via 1,3-dipolar azide-alkyne cycloaddition chemistry and (ii) each copy of the DNA comprises a self-priming moiety, comprising performing the following steps for each nucleic acid residue of the DNA to be sequenced:

(a) contacting the bound DNA with DNA polymerase and four photocleavable fluorescent nucleotide analogues under conditions permitting the DNA polymerase to catalyze DNA synthesis, wherein (i) the nucleotide analogues consist of an analogue of G, an analogue of C, an analogue of T and an analogue of A, so that a nucleotide analogue complementary to the residue being sequenced is bound to the DNA by the DNA polymerase, and (ii) each of the four analogues has a pre-determined fluorescence wavelength which is different than the fluorescence wavelengths of the other three analogues;

(b) removing unbound nucleotide analogues; and (c) determining the identity of the bound nucleotide analogue, thereby determining the sequence of the DNA.

In one embodiment, the instant method further comprises the step of photocleaving the fluorescent moiety from the bound nucleotide analogue following step (c).

In another embodiment of the instant method, the solid substrate is glass or quartz.

In a further embodiment of the instant method, fewer than 100 copies of the DNA, fewer than 20 copies of the DNA, or fewer than five copies of the DNA are bound to the solid substrate.

In still a further embodiment, one copy of the DNA is bound to the solid substrate.

This invention also provides a method for determining the sequence of an RNA, wherein (i) about 1000 or fewer copies of the RNA are bound to a solid substrate via 1,3-dipolar azide-alkyne cycloaddition chemistry and (ii) each copy of the RNA comprises a self-priming moiety, comprising performing the following steps for each nucleic acid residue of the RNA to be sequenced:

(a) contacting the bound RNA with RNA polymerase and four photocleavable fluorescent nucleotide analogues under conditions permitting the RNA polymerase to catalyze RNA synthesis, wherein (i) the nucleotide analogues consist of an analogue of G, an analogue of C, an analogue of U and an analogue of A, so that a nucleotide analogue complementary to the residue being sequenced is bound to the RNA by the RNA polymerase, and (ii) each of the four analogues has a pre-determined fluorescence wavelength which is different than the fluorescence wavelengths of the other three analogues;

(b) removing unbound nucleotide analogues; and (c) determining the identity of the bound nucleotide analogue, thereby determining the sequence of the RNA.

In one embodiment the instant method, further comprises the step of photocleaving the fluorescent moiety from the bound nucleotide analogue following step (c).

In another embodiment of the instant method, the solid substrate is glass or quartz.

In a further embodiment of the instant method, fewer than 100 copies of the RNA, fewer than 20 copies of the RNA, or fewer than five copies of the RNA are bound to the solid substrate.

In still a further embodiment, one copy of the RNA is bound to the solid substrate.

This invention also provides a composition of matter comprising a solid substrate having a DNA bound thereto via 1,3-dipolar azide-alkyne cycloaddition chemistry, wherein (i) about 1000 or fewer copies of the DNA are bound to the solid substrate, and (ii) each copy of the DNA comprises a self-priming moiety.

This invention also provides a composition of matter comprising a solid substrate having an RNA bound thereto via 1,3-dipolar azide-alkyne cycloaddition chemistry, wherein (i) about 1000 or fewer copies of the RNA are bound to the solid substrate, and (ii) each copy of the RNA comprises a self-priming moiety.

In one embodiment of the instant methods and compositions of matter, the number of DNA or RNA copies bound to the solid substrate exceeds 1000, and can be, for example, about $10^4$, $10^5$, $10^6$, $10^7$, $10^8$, $10^9$, or greater.

This invention also provides a compound having the structure:

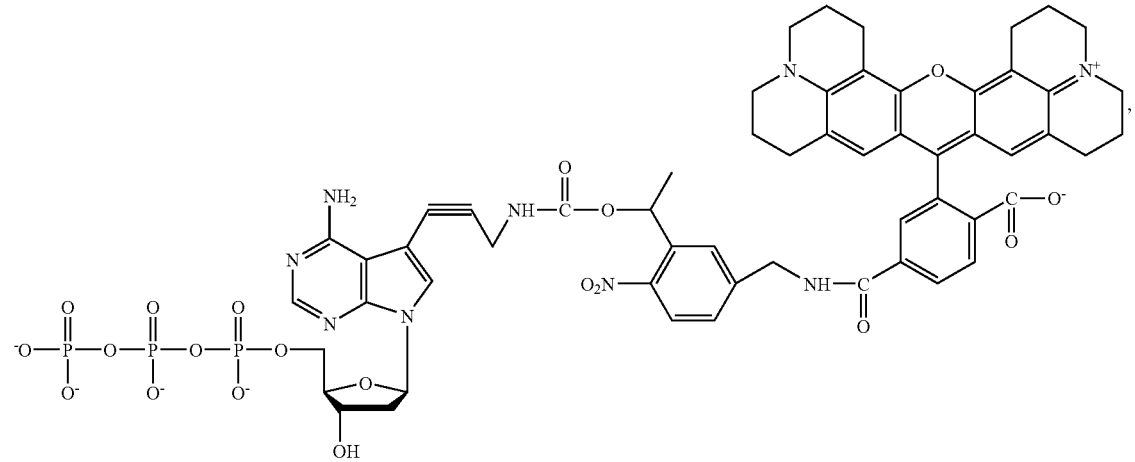

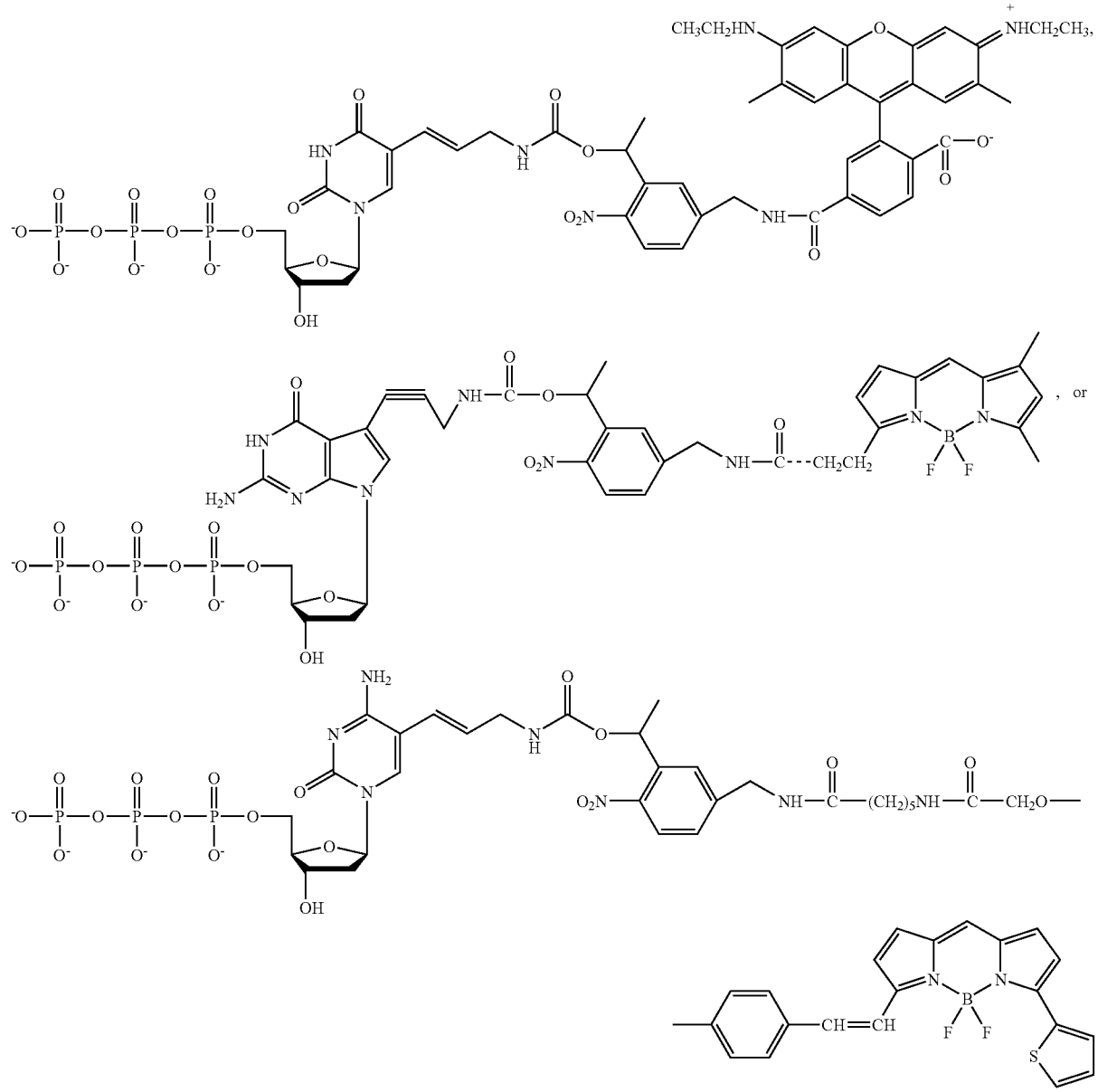

This invention will be better understood by reference to the Experimental Details which follow, but those skilled in the art will readily appreciate that the specific experiments detailed are only illustrative of the invention as described more fully in the claims which follow thereafter.

Experimental Details

Synopsis

Here, the procedure for performing SBS on a chip using a synthetic DNA template and photocleavable pyrimidine nucleotides (C and U) is disclosed (also see 16). In addition, the design and synthesis of 4 photocleavable nucleotide analogues (A, C, G, U), each of which contains a unique fluorophore with a distinct fluorescence emission is described. Initially, it was established that these nucleotides are good substrates for DNA polymerase in a solution-phase DNA extension reaction and that the fluorophore can be removed with high speed and efficiency by laser irradiation ($\lambda\sim 355$ nm). SBS was then performed using these 4 photocleavable nucleotide analogues to identify the sequence of a DNA template immobilized on a chip. The DNA template was produced by PCR using an azido-labeled primer, and was immobilized on the surface of the chip with 1,3-dipolar azide-alkyne cycloaddition chemistry. A self-priming moiety was then covalently attached to the DNA template by enzymatic ligation to allow the polymerase reaction to proceed on the DNA immobilized on the surface. This is the first report of using a complete set of photocleavable fluorescent nucleotides for 4-color DNA sequencing by synthesis.

Introduction

A 4-color DNA sequencing by synthesis (SBS) on a chip using four photocleavable fluorescent nucleotide analogues (dGTP-PC-Bodipy-FL-510, dUTP-PC-R6G, dATP-PC-ROX, and dCTP-PC-Bodipy-650) is disclosed herein. Each nucleotide analogue consists of a different fluorophore attached to the 5-position of the pyrimidines (C and U) and the 7-position of the purines (G and A) through a photocleavable 2-nitrobenzyl linker. After verifying that these nucleotides could be successfully incorporated into a growing DNA strand in a solution-phase polymerase reaction and the fluorophore could be cleaved using laser irradiation (λ~355 nm) in 10 seconds, an SBS reaction was performed on a chip which contained a self-priming DNA template covalently immobilized using 1,3-dipolar azide-alkyne cycloaddition. The DNA template was produced by a polymerase chain reaction using an azido-labeled primer and the self-priming moiety was attached to the immobilized DNA template by enzymatic ligation. Each cycle of SBS consisted of the incorporation of the photocleavable fluorescent nucleotide into the DNA, detection of the fluorescent signal and photocleavage of the fluorophore. The entire process was repeated to identify 12 continuous bases in the DNA template. These results demonstrate that photocleavable fluorescent nucleotide analogues can be incorporated accurately into a growing DNA strand during a polymerase reaction in solution phase as well as on a chip. Moreover, all 4 fluorophores can be detected and then efficiently cleaved using near-UV irradiation, thereby allowing continuous identification of the DNA template sequence.

Figure 7:
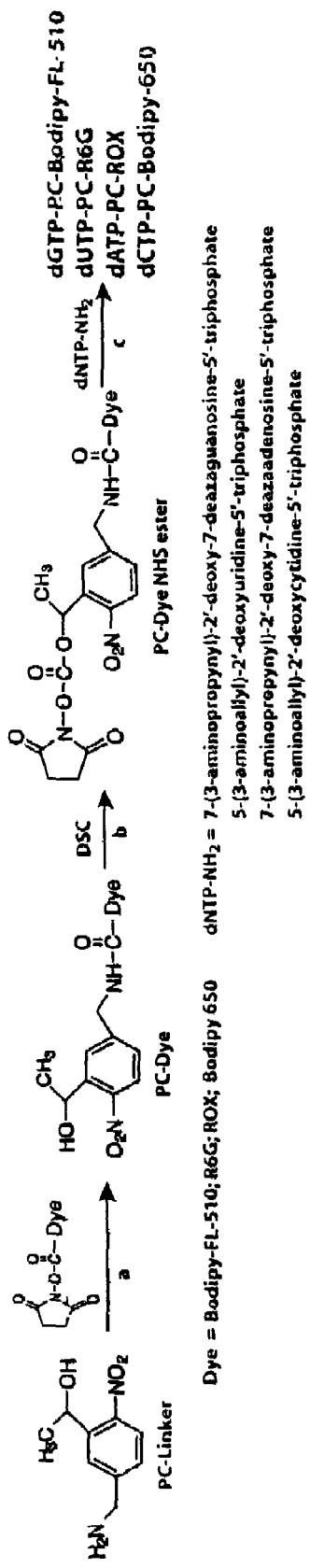
FIG. 7. Synthesis of photocleavable fluorescent nucleotides. (a) acetonitrile or DMF/1 M NaHCO₃ solution; (b) N,N'-disuccinimidyl carbonate (DSC), triethylamine; (c) 0.1 M Na₂CO₃/NaHCO₃ aqueous buffer (pH 8.5-8.7).

To demonstrate the feasibility of carrying out DNA sequencing by synthesis on a chip, four photocleavable fluorescent nucleotide analogues (dGTP-PC-Bodipy-FL-510, dUTP-PC-R6G, dATP-PC-ROX, and dCTP-PC-Bodipy-650) (FIG. 6) were synthesized according to the scheme shown in FIG. 7 using a similar procedure as reported previously (16). Modified DNA polymerases have been shown to be highly tolerant to nucleotide modifications with bulky groups at the 5-position of pyrimidines (C and U) and the 7-position of purines (A and G) (17, 18). Thus, each unique fluorophore was attached to the 5 position of C/U and the 7 position of A/G through a photocleavable 2-nitrobenzyl linker.

Figure 1:
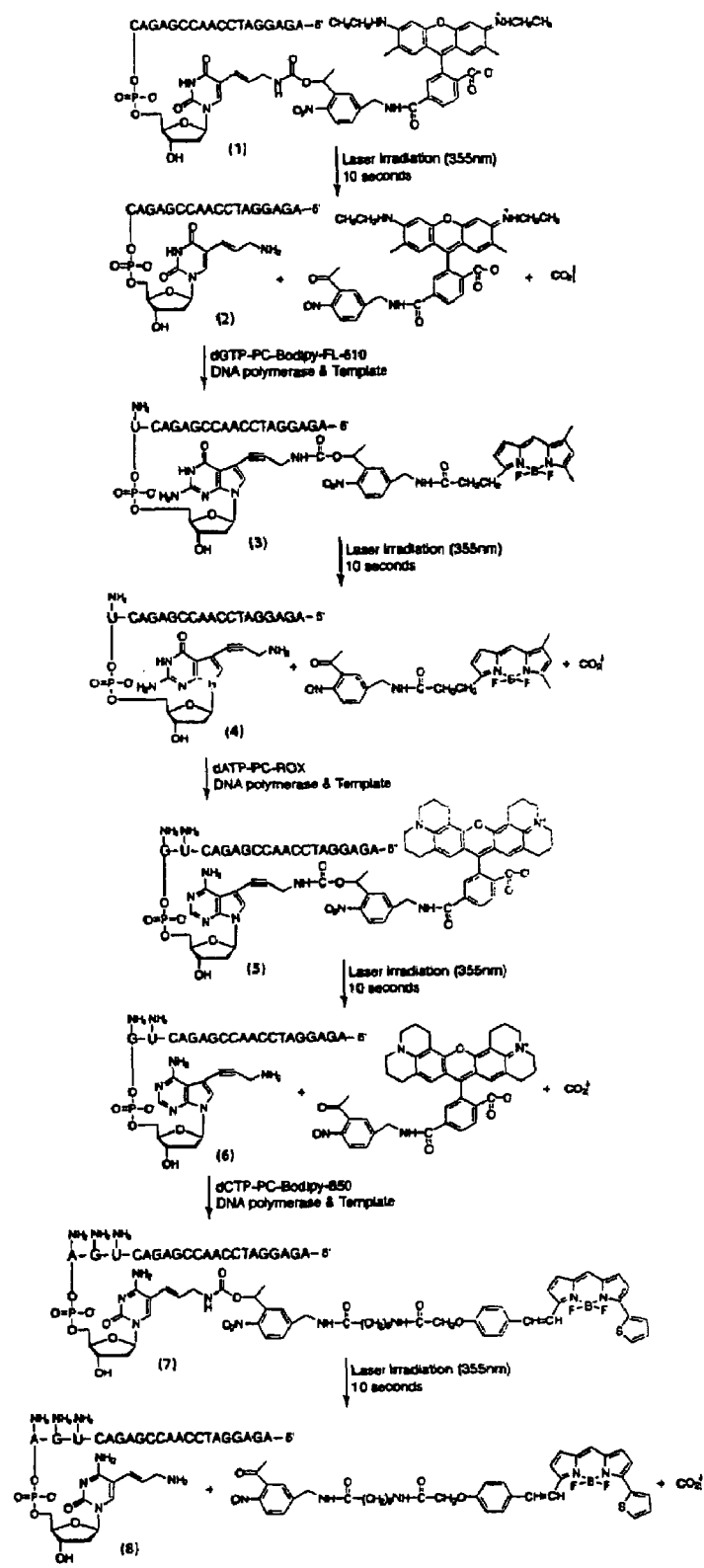
FIG. 1: DNA extension reaction performed in solution phase to characterize the 4 different photocleavable fluorescent nucleotide analogues (dUTP-PC-R6G, dGTP-PC-Bodipy-FL-510, dATP-PC-ROX, dCTP-PC-Bodipy-650). After each extension reaction, the DNA extension product (SEQ ID NOs. 1-4) is purified by HPLC for MALDI-TOF MS measurement to verify that it is the correct extension product. Photolysis is performed to produce a DNA product that is used as a primer for the next DNA extension reaction.
Figure 2:
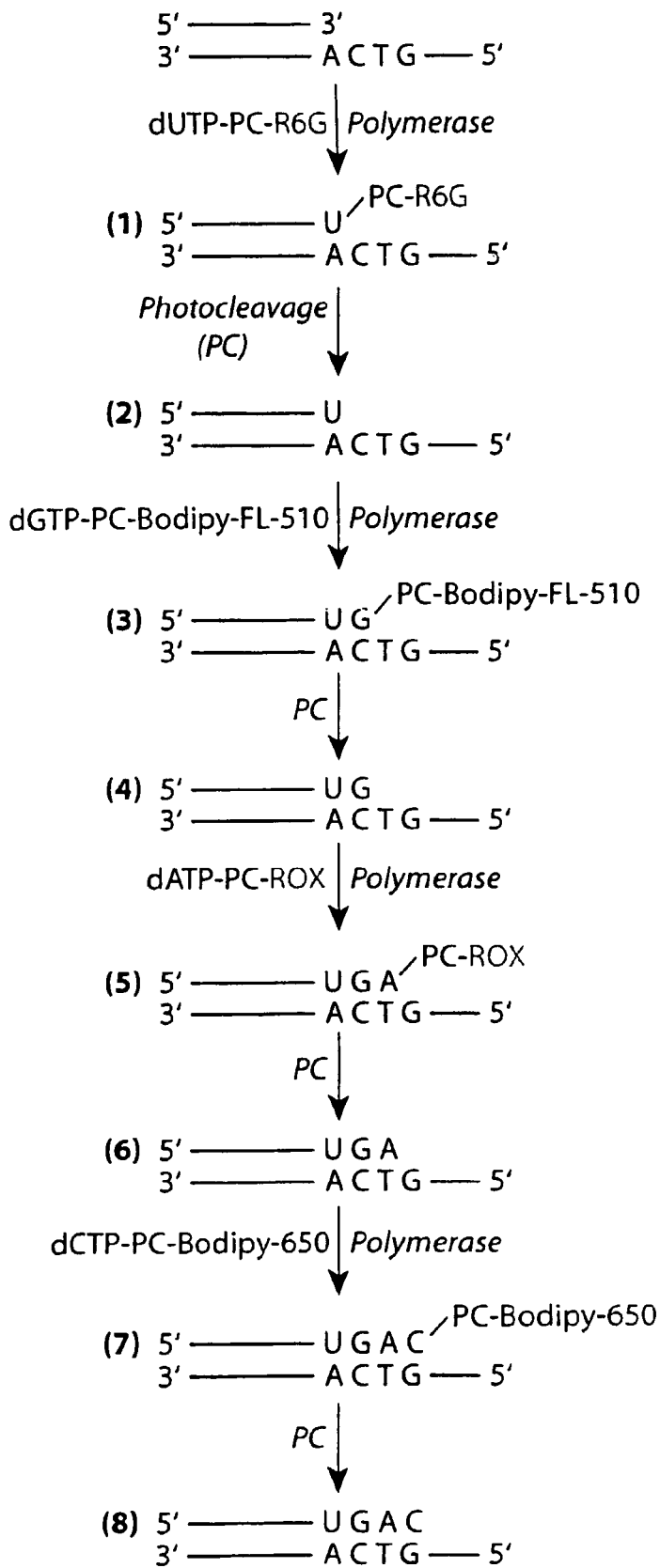
FIG. 2. Polymerase extension scheme. Primer extended with dUTP-PC-R6G (1), and its photocleavage product 2; Product 2 extended with dGTP-PC-Bodipy-FL-510 (3), and its photocleavage product 4; Product 4 extended with dATP-PC-ROX (5), and its photocleavage product 6; Product 6 extended with dCTP-PC-Bodipy-650 (7), and its photocleavage product 8. After 10 seconds of irradiation with a laser at 355 nm, photocleavage is complete with all the fluorophores cleaved from the extended DNA products.
Figure 3:
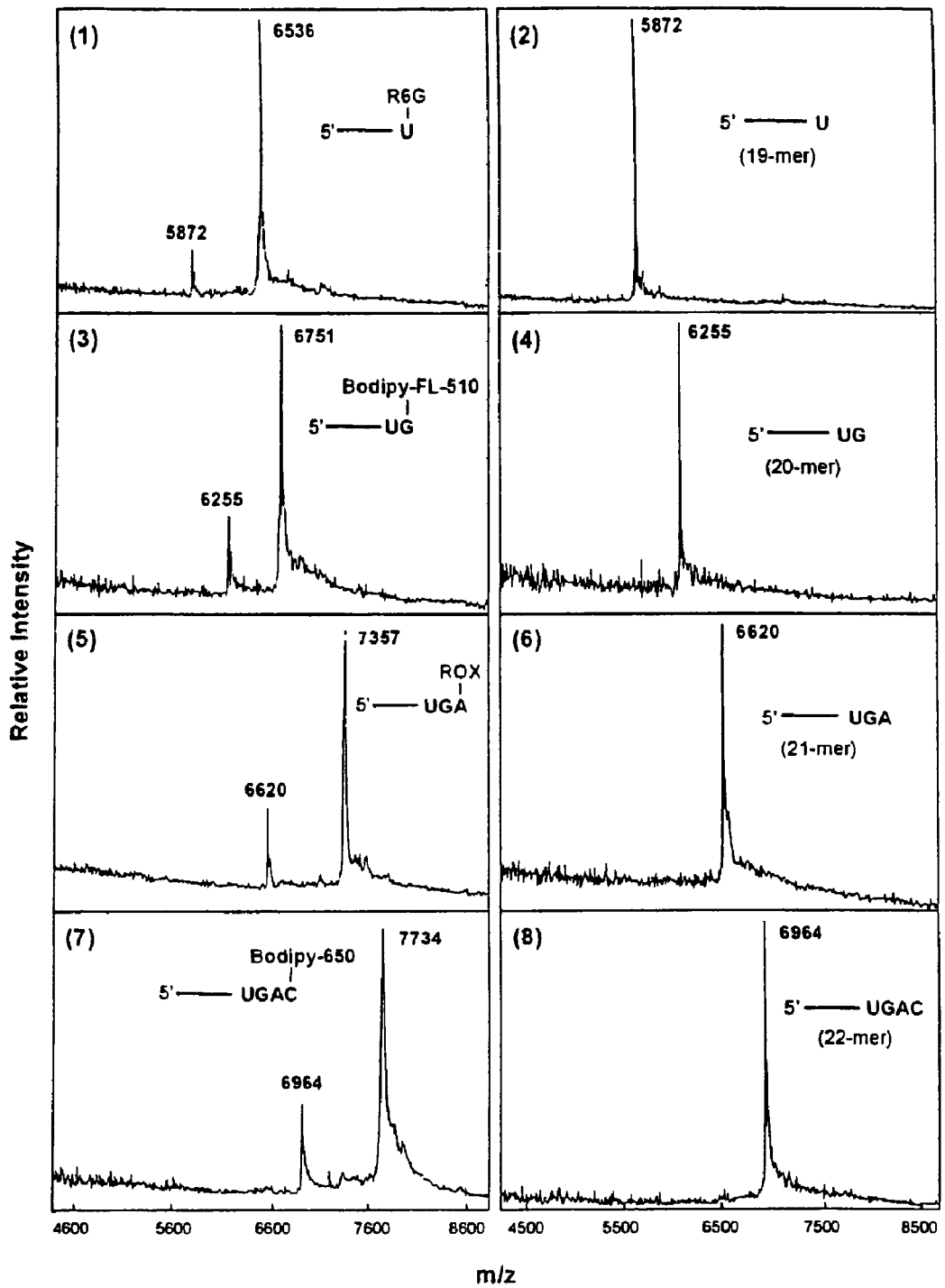
FIG. 3. Panels (1)-(8). MALDI-TOF MS spectra of the four consecutive extension products and their photocleavage products. Primer extended with dUTP-PC-R6G (1), and its photocleavage product 2; Product 2 extended with dGTP-PC-Bodipy-FL-510 (3), and its photocleavage product 4; Product 4 extended with dATP-PC-ROX (5), and its photocleavage product 6; Product 6 extended with dCTP-PC-Bodipy-650 (7), and its photocleavage product 8. After 10 seconds of irradiation with a laser at 355 nm, photocleavage is complete with all the fluorophores cleaved from the extended DNA products.

In order to verify that these fluorescent nucleotides are incorporated accurately in a base-specific manner in a polymerase reaction, four continuous steps of DNA extension and photocleavage by near UV irradiation were carried out in solution as shown in FIG. 1. This allows the isolation of the DNA product at each step for detailed molecular structure characterization as shown in FIG. 2. The first extension product 5'-U(PC-R6G)-3' 1 was purified by HPLC and analyzed using MALDI-TOF MS [FIG. 3]. This product was then irradiated at 355 nm using an Nd-YAG laser for 10 seconds and the photocleavage product 2 was also analyzed using MALDI-TOF MS [FIG. 3]. Near UV light absorption by the aromatic 2-nitrobenzyl linker causes reduction of the 2-nitro group to a nitroso group and an oxygen insertion into the carbon-hydrogen bond followed by cleavage and decarboxylation (19). As can be seen from FIG. 3, Panel 1, the MALDI-TOF MS spectrum consists of a distinct peak at m/z 6536 corresponding to the DNA extension product 5'-U(PC-R6G)-3' (1), which confirms that the nucleotide analogue can be incorporated base specifically by DNA polymerase into a growing DNA strand. The small peak at m/z 5872 corresponding to the photocleavage product is due to the partial cleavage caused by the nitrogen laser pulse (337 nm) used in MALDI ionization. For photocleavage, a Nd-YAG laser was used to irradiate the DNA product carrying the fluorescent nucleotide for 10 seconds at 355 nm to cleave the fluorophore from the DNA extension product. FIG. 3, Panel 2, shows the photocleavage result of the above DNA product. The peak at m/z 6536 has completely disappeared while the peak corresponding to the photocleavage product 5'-U (2) appears as the sole dominant peak at m/z 5872, which establishes that laser irradiation completely cleaves the fluorophore with high speed and efficiency without damaging the DNA. The next extension reaction was carried out using this photocleaved DNA product as a primer along with dGTP-PC-Bodipy-FL-510 to yield an extension product 5'-UG(PC-Bodipy-FL-510)-3' (3). As described above, the extension product 3 was purified, analyzed by MALDI-TOF MS producing a dominant peak at m/z 6751 [FIG. 3, Panel 3], and then photocleaved for further MS analysis yielding a single peak at m/z 6255 (product 4) [FIG. 3, Panel 4]. The third extension using dATP-PC-ROX to yield 5'-UGA(PC-ROX)-3' (5), the fourth extension using dCTP-PC-Bodipy-650 to yield 5'-UGAC (PC-Bodipy-650)-3' (7) and their photocleavage to yield products 6 and 8 were similarly carried out and analyzed by MALDI-TOF MS as shown in FIG. 3, Panels 5-8. These results demonstrate that the above-synthesized four photocleavable fluorescent nucleotide analogues can successfully incorporate into the growing DNA strand in a polymerase reaction, and the fluorophore can be efficiently cleaved by near UV irradiation, which makes it feasible to use them for SBS on a chip.

Figure 4:
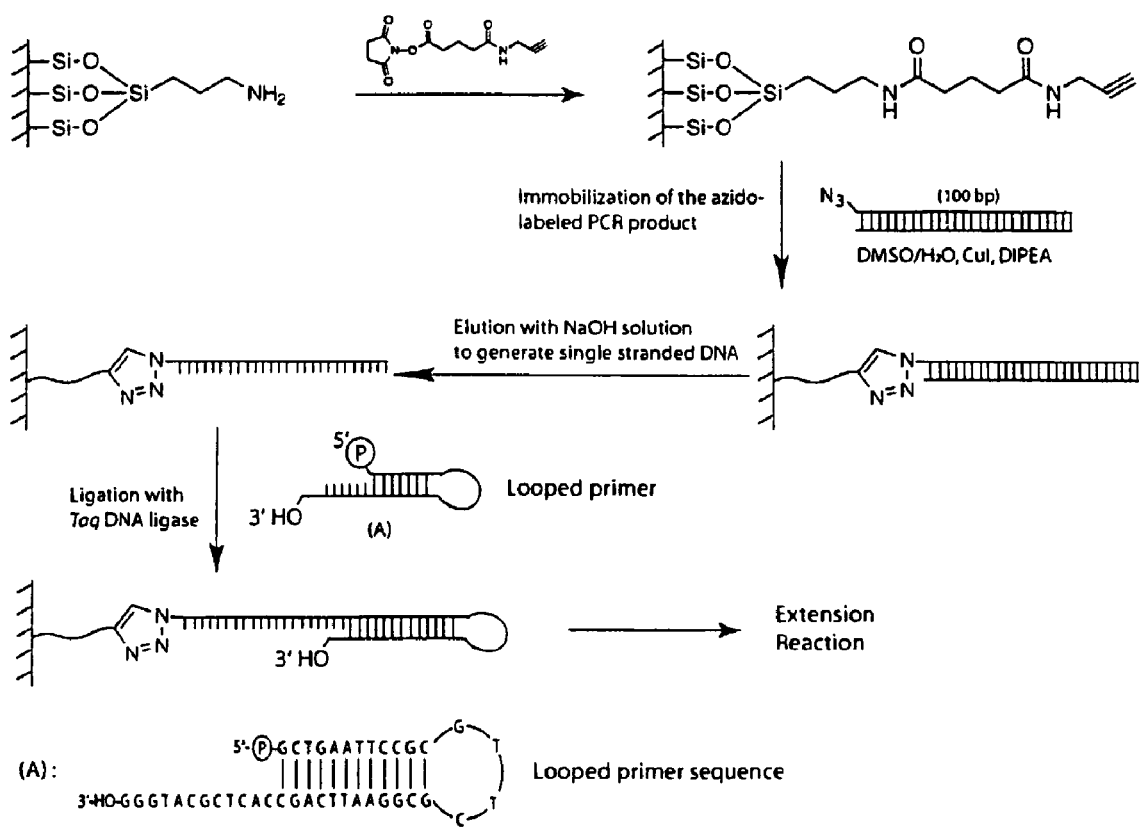
FIG. 4. Immobilization of an azido-labeled PCR product on an alkynyl-functionalized surface and a ligation reaction between the immobilized single-stranded DNA template and a loop primer to form a self-priming DNA moiety on the chip. The sequence of the loop primer is shown in (A).

The photocleavable fluorescent nucleotide analogues were then used in an SBS reaction to identify the sequence of the DNA template immobilized on a solid surface as shown in FIG. 4. A site-specific 1,3-dipolar cycloaddition coupling chemistry was used to covalently immobilize the azido-labeled double-stranded PCR products on the alkynyl-functionalized surface in the presence of a Cu(I) catalyst. Previously, we have shown that DNA is successfully immobilized on the glass surface by this chemistry and evaluated the functionality of the surface-bound DNA and the stability of the array using a primer extension reaction (16). The surface-immobilized double stranded PCR product was denatured using a 0.1 M NaOH solution to remove the complementary strand without the azido group, thereby generating a single-stranded PCR template on the surface. Then, a 5'-phosphorylated self-priming moiety (loop primer) was ligated to the 3'-end of the above single stranded DNA template using Taq DNA ligase (20). The structure of the loop primer was designed to bear a thermally stable loop (21) and stem sequence with a melting temperature of 89° C. The 12-bp overhanging portion of the loop primer was made complementary to the 12-bp sequence of the template at its 3' end to allow the Taq DNA ligase to seal the nick between the 5'-phosphate group of the loop primer and the 3'-hydroxyl group of the single-stranded DNA template. This produces a unique DNA moiety that can self-prime for the synthesis of a complementary strand. The ligation was found to be in quantitative yield in a parallel solution-phase reaction using the same primer and single-stranded DNA template.

Figure 5:
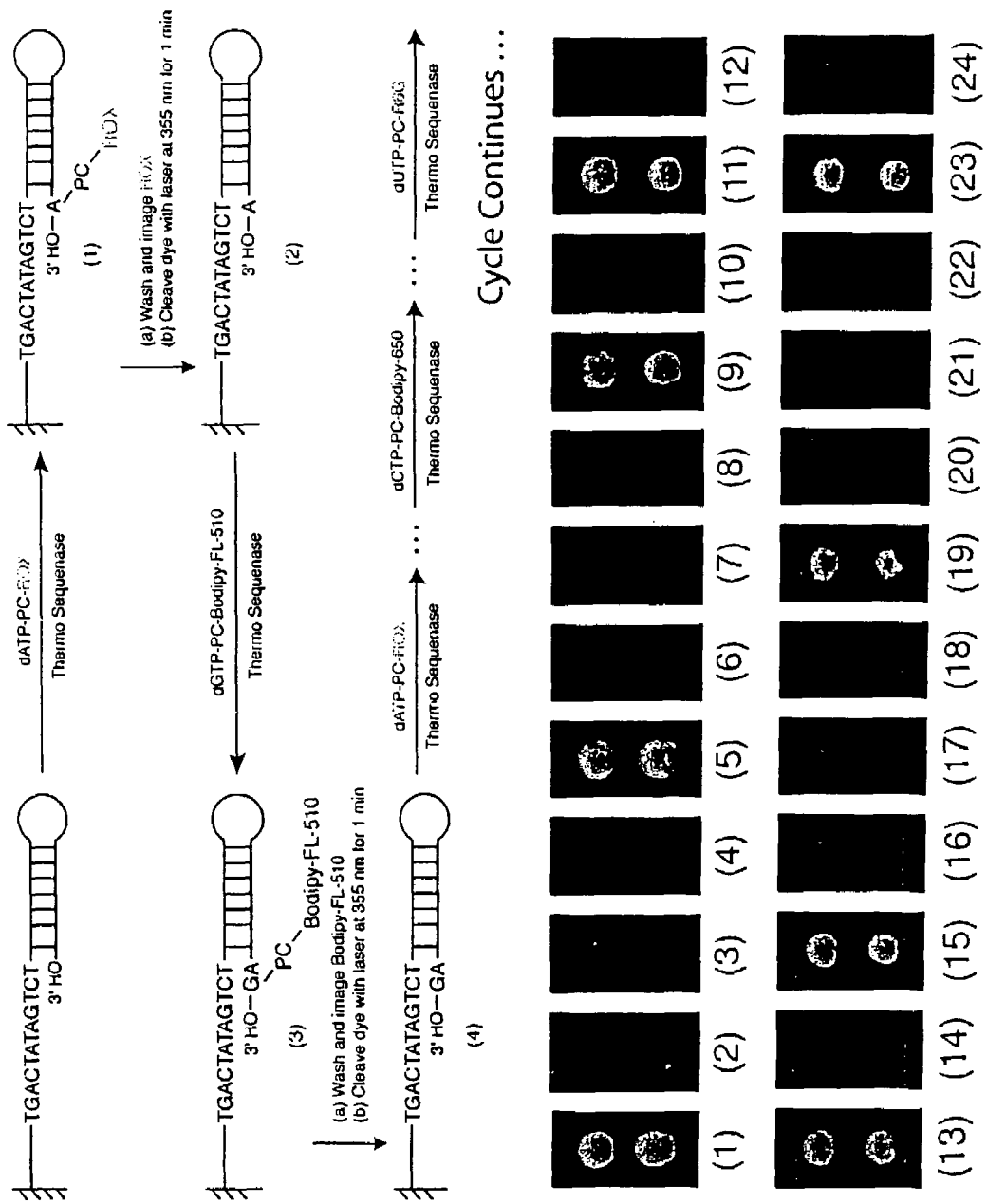
FIG. 5. Schematic representation of SBS on a chip using four PC fluorescent nucleotides (Upper panel) and the scanned fluorescence images for each step of SBS on a chip (Lower panel). (1) Incorporation of dATP-PC-ROX; (2) Photocleavage of PC-ROX; (3) Incorporation of dGTP-PC-Bodipy-FL-510; (4) Photocleavage of PC-Bodipy-FL-510; (5) Incorporation of dATP-PC-ROX; (6) Photocleavage of PC-ROX; (7) Incorporation of dCTP-PC-Bodipy-650; (8) Photocleavage of PC-Bodipy-650; (9) Incorporation of dUTP-PC-R6G; (10) Photocleavage of PC-R6G; (11) Incorporation of dATP-PC-ROX; (12) Photocleavage of PC-ROX; (13) Incorporation of dUTP-PC-R6G; (14) Photocleavage of PC-R6G; (15) Incorporation of dATP-PC-ROX; (16) Photocleavage of PC-ROX; (17) Incorporation of dGTP-PC-Bodipy-FL-510; (18) Photocleavage of PC-Bodipy-FL-510; (19) Incorporation of dUTP-PC-R6G; (20) Photocleavage of PC-R6G; (21) Incorporation of dCTP-PC-Bodipy-650; (22) Photocleavage of PC-Bodipy-650; (23) Incorporation of dATP-PC-ROX; (24) Photocleavage of PC-ROX.

The principal advantage offered by the use of a self-priming moiety as compared to using separate primers and templates is that the covalent linkage of the primer to the template in the self-priming moiety prevents any possible dissociation of the primer from the template under vigorous washing conditions. Furthermore, the possibility of mis-priming is considerably reduced and a universal loop primer can be used for all the templates allowing enhanced accuracy and ease of operation. SBS was performed on the chip-immobilized DNA template using the 4 photocleavable fluorescent nucleotide analogues, see FIG. 5. The structure of the self-priming DNA moiety is shown schematically in the upper panel, with the first 12 nucleotide sequence immediately after the priming site. The sequencing reaction on the chip was initiated by extending the self-priming DNA using dATP-PC-ROX (complementary to the T on the template), and Thermo Sequenase DNA polymerase. After washing, the extension of the primer by a single fluorescent nucleotide was confirmed by observing an orange signal (the emission signal from ROX) in a microarray scanner [FIG. 5, (1)]. After detection of the fluorescent signal, the surface was irradiated at 355 nm for 1 min using an Nd-YAG laser to cleave the fluorophore. The surface was then washed, and a negligible residual fluorescent signal was detected to confirm complete photocleavage of the fluorophore [FIG. 5, (2)]. This was followed by incorporation of the next fluorescent nucleotide complementary to the subsequent base on the template. The entire process of incorporation, detection and photocleavage was performed multiple times using the four photocleavable fluorescent nucleotide analogues to identify 12 successive bases in the DNA template. The integrated fluorescence intensity on the spot, obtained from the scanner software, indicated that the incorporation efficiency was over 90% and more than 97% of the original fluorescence signal was removed by photocleavage. A negative control experiment consisting of incubating the self-priming DNA moiety with dATP-PC-ROX in the absence of DNA polymerase and washing the surface showed that negligible fluorescence remained as compared to that of FIG. 5, (1).

In summary, four photocleavable fluorescent nucleotide analogues have been synthesized and characterized and have been used to produce 4-color DNA sequencing data on a chip. These nucleotides have been shown to be excellent substrates for the DNA polymerase and the fluorophore could be cleaved efficiently using near UV irradiation. This is important with respect to enhancing the speed of each cycle in SBS for high throughput DNA analysis. Also, a PCR-amplified DNA template can be ligated with a self-priming moiety demonstrated that and its sequence can be accurately identified in a DNA polymerase reaction on a chip, indicating that a PCR product from any organism can be potentially used as a template for the SBS system in the future. The modification of the 3'-OH of the photocleavable fluorescent nucleotide with a small chemical group to allow reversible termination may be considered. The library of photocleavable fluorescent nucleotides reported here will also facilitate single molecule DNA sequencing approaches.

Materials and Methods

All chemicals were purchased from Sigma-Aldrich unless otherwise indicated. $^1$H NMR spectra were recorded on a Bruker 400 spectrometer. High-resolution MS (HRMS) data were obtained by using a JEOL JMS HX 110A mass spectrometer. Mass measurement of DNA was made on a Voyager DE matrix-assisted laser desorption ionization-time-of-flight (MALDI-TOF) mass spectrometer (Applied Biosystems). Photolysis was performed using a Spectra Physics GCR-150-30 Nd-YAG laser that generates light pulses at 355 nm (ca. 50 mJ/pulse, pulse length ca. 7 ns) at a frequency of 30 Hz with a light intensity at ca. 1.5 W/cm$^2$. The scanned fluorescence emission images were obtained by using a ScanArray Express scanner (Perkin-Elmer Life Sciences) equipped with four lasers with excitation wavelengths of 488, 543, 594, and 633 nm and emission filters centered at 522, 570, 614, and 670 nm.

Synthesis of Photocleavable Fluorescent Nucleotides

Photocleavable fluorescent nucleotides dGTP-PC-Bodipy-FL-510, dUTP-PC-R6G, dATP-PC-ROX and dCTP-PC-Bodipy-650 (FIG. 6) were synthesized according to FIG. 7 using a similar method as reported (16). A photocleavable linker (PC-Linker) 1-[5-(aminomethyl)-2-nitrophenyl]ethanol was reacted with the NHS ester of the corresponding fluorescent dye to produce an intermediate PC-Dye, which was converted to a PC-Dye NHS ester by reacting with N, N'-disuccinimidyl carbonate. The coupling reaction between the different PC-Dye NHS esters and the amino nucleotides (dATP-NH$_2$ and dGTP-NH$_2$ from Perkin-Elmer; dUTP-NH$_2$ from Sigma; dCTP-NH$_2$ from TriLink BioTechnologies) produced the 4 photocleavable fluorescent nucleotides.

The synthesis of the photocleavable fluorescent nucleotide dCTP-PC-Bodipy-650 was reported (Seo, T. S., Bai, X., Ruparel, H., Li, Z., Turro, N. J. & Ju, J. (2004) *Proc. Natl. Acad. Sci. USA* 101, 5488 5493). dUTP-PC-R6G, dGTP-PC-Bodipy-FL-510 and dATP-PC-ROX were prepared with a similar procedure as shown in FIG. 7.

A general procedure for the synthesis of PC—Dye: 1-[5-(Aminomethyl)-2-nitrophenyl]ethanol (2) (PC-Linker, 5 mg, 26 µmol) was dissolved in 550 µl of acetonitrile (for Bodipy) or DMF (for R6G and ROX) and then mixed with 100 µl of 1 M NaHCO3 aqueous solution. A solution of the NHS ester of the corresponding fluorophore (Molecular Probes) (13 µmol) in 400 pl of acetonitrile or DMF was added slowly to the above reaction mixture and then stirred for 5 h at room temperature. The resulting reaction mixture was purified on a preparative silica-gel TLC plate (CHCl$_3$/CH$_3$OH, 4/1 for Bodipy, 1/1 for R6G and ROX) to yield pure PC-Dye. PC-R6G: (92% yield) $_1$NMR (400 z, CD$_3$ D) 8.17 (d, 2H), 7.87(d, 2H),7.76 (d, 1H), 7.45(d, 1H), 7.04 (s, 2H), 6.89 (s, 2H), 5.34 (q, 1H), 4.70 (s, 2H), 3.52(q, 4H), 2.14 (s, 6H), 1.47(d, 3H), 1.35 (t, 6H). HRMS (FAB$_+$) m/z: calcd for C$_{36}$H$_{37}$N$_4$O$_7$ (M+H$_+$), 637.2622; found, 637.2643. PC-ROX: (90% yield) $_1$NMR (400 z, CD$_3$ D) 8.11 (d, 2H), 7.88 (m, 2H), 7.69 (d, 1H), 7.45 (dd, 1H), 6.79(s, 1H), 5.36(q, 1H), 4.69 (s, 2H), 3.50 (m, 8H), 3.08(t, 4H), 2.73 (t, 4H), 2.11 (t, 4H), 1.95 (t, 4H), 1.47 (d, 3H). HRMS (FAB$_+$) m/z: calcd for C$_{42}$H$_{41}$N$_4$O$_7$ (M+H$_+$), 713.2975; found, 713.2985. PC-Bodipy-FL-510 was reported (Li, Z., Bai, X., Ruparel, H., Kim, S., Turro, N. J. & Ju, J. (2003) *Proc. Natl. Acad. Sci. USA* 100, 414-419.)

A general procedure for the synthesis of PC-Dye NHS ester: N,N'-disuccinimidyl carbonate (4.27 mg, 17 µmol) and triethylamine (4.6 µl, 33 µmol) were added to a solution of PC-Dye (11 µmol) in 200 µl of dry acetonitrile or DMF. The reaction mixture was stirred under argon at room temperature for 6 h. The solvent was removed under vacuum, and the residue was immediately purified by flash column chromatography (CH$_2$Cl$_2$/CH$_3$OH, 4/1). PC-R6G NHS ester: (28% yield) $_1$H NMR (400 MHz, CD$_3$OD) 8.15 (s, 2H), 8.03 (d, 1H), 7.78 (m, 1H), 7.71 (d, 1H), 7.56 (dd, 2H), 7.02 (m, 2H), 6.86 (m, 2H), 6.30 (q, 1H), 4.78 (d, 1H), 4.67 (d, 1H), 3.51 (q, 4H), 2.67 (s, 4H), 2.12 (s, 6H), 1.73 (d, 3H), 1.35 (t, 6H). HRMS (FAB$_+$) m/z: calculated for C$_{41}$H$_{40}$O$_{11}$N$_5$ (M+H$_+$), 778.2724; found, 778.2731. PC-ROX NHS ester: (35% yield) $_1$H NMR3 (400 MHz, CD$_3$OD) 8.09 (m, 2H), 8.02 (d, 1H), 7.69-7.75(m, 2H), 7.54 (dd, 2H), 6.77 (m,2H), 6.30 (q, 1H), 4.78 (d, 1H), 4.66 (d, 1H), 3.47-3.57 (m, 8H), 3.04-3.10 (m, 4H), 2.64-2.72 (m, 8H), 2.06-2.14 (m, 4H), 1.90-1.98 (m, 4H), 1.74 (d, 3H). HRMS (FAB$_+$) m/z: calcd for C$_{47}$H$_{44}$O$_{11}$N$_5$ (M+H$_+$), 854.3037; found, 854.3069. PC-Bodipy-FL-510 NHS ester was reported (Li, Z., Bai, X., Ruparel, H., Kim, S., Turro, N. J. & Ju, J. (2003) *Proc. Natl. Acad. Sci. USA* 100, 414-419.)

A general procedure for the synthesis of photocleavable fluorescent nucleotides dUTP-PCR6G, dGTP-PC-Bodipy-FL-510 and dATP-PC-ROX PC-Dye NHS ester (30 µmol) in 300 µl of acetonitrile or DMF was added to a solution of amino nucleotide dNTP-NH$_2$ (1 µmol) in 300 µl of 0.1 M Na$_2$CO$_3$—NaHCO$_3$ buffer (pH 8.5-8.7). The reaction mixture was stirred at room temperature for 3 h. A preparative silica-gel TLC plate was used to separate the unreacted PCDye NHS ester from the fractions containing final photocleavable fluorescent nucleotides (CHCl₃/CH₃OH, 1/1). The product was concentrated further under vacuum and purified with reverse-phase HPLC on a 150 4.6-mm C18 column to obtain the pure product. Mobile phase: A, 8.6 mM triethylamine/100 mM hexafluoroisopropyl alcohol in water (pH 8.1); B, methanol. Elution was performed with 100% A isocratic over 10 min followed by a linear gradient of 0-50% B for 20 min and then 50% B isocratic over another 20 min.

DNA Polymerase Reaction using 4 Photocleavable Fluorescent Nucleotide Analogues in Solution The four nucleotide analogues, dGTP-PC-Bodipy-FL-510, dUTP-PC-R6G, dATP-PC-ROX and dCTP-PC-Bodipy-650 were characterized by performing four continuous DNA-extension reactions sequentially using a primer (5'-AGAGGATCCAACCGAGAC-3') (SEQ ID NO:5) and a synthetic DNA template(5'-GTGTACATCAACATCAC-CTACCACCATGTCAGTCTCGGTTGGAT-CCTCTAT-TGTGTCCGG-3') (SEQ ID NO:6) corresponding to a portion of exon 7 of the human p53 gene (FIG. 1). The four nucleotides in the template immediately adjacent to the annealing site of the primer were 3'-ACTG-5'. First, a polymerase extension reaction using dUTP-PC-R6G along with the primer and the template was performed producing a single base extension product. The reaction mixture for this, and all subsequent extension reactions, consisted of 80 pmol of template, 50 pmol of primer, 80 pmol of the particular photocleavable fluorescent nucleotide, 1× Thermo Sequenase reaction buffer, and 4 U of Thermo Sequenase DNA polymerase (Amersham Biosciences) in a total volume of 20 μL. The reaction consisted of 25 cycles at 94° C. for 20 sec, 48° C. for 40 sec, and 60° C. for 75 sec. Subsequently, the extension product was purified by using reverse-phase HPLC. An Xterra MS C18 (4.6×50-mm) column (Waters) was used for the HPLC purification. Elution was performed over 120 minutes at a flow rate of 0.5 mL/min with the temperature set at 50° C. by using a linear gradient (12-34.5%) of methanol in a buffer consisting of 8.6 mM triethylamine and 100 mM hexafluoroisopropyl alcohol (pH 8.1). The fraction containing the desired DNA product was collected and freeze-dried for analysis using MALDI-TOF mass spectrometry. For photocleavage, the purified DNA extension product bearing the fluorescent nucleotide analogue was resuspended in 200 μL of deionized water. The mixture was irradiated for 10 seconds in a quartz cell with path lengths of 1.0 cm employing a Nd-YAG laser at 355 nm and then analyzed by MALDI-TOF MS. After photocleavage, the DNA product with the fluorophore removed was used as a primer for a second extension reaction using dGTP-PC-Bodipy-FL-510. The second extended product was then purified by HPLC and photolyzed. The third extension using dATP-PC-ROX and the fourth extension using dCTP-PC-Bodipy-650 were carried out in a similar manner using the previously extended and photocleaved product as the primer.

PCR Amplification to Produce Azido-Labeled DNA Template

An azido-labeled PCR product was obtained using a 100-bp template (5'-AGCGACTGCTATCATGTCATATC-GACGTGCTCACTAGCTCTAC ATATGCGTGCGTGAT-CAGATGACGTATCGATGCTGACTATAGTCTCCCAT GCGAGTG-3'), (SEQ ID NO:7) a 24-bp azido-labeled forward primer (5'-N₃-AGCGACTGCTATCATGTCATATCG-3'), (SEQ ID NO:8) and a 24-bp unlabeled reverse primer (5'-CACTCGCATGGGAGACTATAGTCA-3'). (SEQ ID NO: 9) In a total reaction volume of 50 μL, 1 pmol of template and 30 pmol of forward and reverse primers were mixed with 1 U of AccuPrime Pfx DNA polymerase and 5 μL of 10× AccuPrime Pfx reaction mix (Invitrogen) containing 1 mM of MgSO₄ and 0.3 mM of dNTP. The PCR reaction consisted of an initial denaturation step at 95° C. for 1 min, followed by 38 cycles at 94° C. for 15 sec, 63° C. for 30 sec, 68° C. for 30 sec. The product was purified using a 96 QIAquick multiwell PCR purification kit (Qiagen) and the quality was checked using 2% agarose gel electrophoresis in 1× TAE buffer. The concentration of the purified PCR product was measured using a Perkin-Elmer Lambda 40 UV-Vis spectrophotometer.

Construction of a Self-Priming DNA Template on a Chip by Enzymatic Ligation

The amino-modified glass slide (Sigma) was functionalized to contain a terminal alkynyl group as described previously (16). The azido-labeled DNA product generated by PCR was dissolved in DMSO/H₂O (1/3, v/v) to obtain a 20 μM solution. 5 μL of the DNA solution was mixed with CuI (10 nmol, 100 eq.) and N,N-diisopropyl-ethylamine (DIPEA) (10 nmol, 100 eq.) and then spotted onto the alkynyl-modified glass surface in the form of 6 μL drops. The glass slide was incubated in a humid chamber at room temperature for 24 hr, washed with deionized water (dH₂O) and SPSC buffer (50 mM sodium phosphate, 1 M NaCl, pH 6.5) for 1 hr (16), and finally rinsed with dH₂O. To denature the double stranded PCR-amplified DNA to remove the non-azido-labeled strand, the glass slide was immersed into 0.1 M NaOH solution for 10 min and then washed with 0.1 M NaOH and dH₂O, producing a single stranded DNA template that is immobilized on the chip. For the enzymatic ligation of a self-priming moiety to the immobilized DNA template on the chip, a 5'-phosphorylated 40-bp loop primer (5'-PO3-GCTGAATTCCGCGT-TCGCGGAATTCAGCCACTCGCATGGG-3') (SEQ ID NO:10) was synthesized. This primer contained a thermally stable loop sequence 3'-G(CTTG)C-5', a 12-bp stem, and a 12-bp overhanging end that would be annealed to the immobilized single stranded template at its 3'-end. A 10 μL solution consisting of 100 pmol of the primer, 10 U of Taq DNA ligase, 0.1 mM NAD, and 1× reaction buffer (New England Biolabs) was spotted onto a location of the chip containing the immobilized DNA and incubated at 45° C. for 4 hr. The glass slide was washed with dH₂O, SPSC buffer, and again with dH₂O. The formation of a stable hairpin was ascertained by covering the entire surface with 1× reaction buffer (26 mM TrisHCl/6.5 mM MgCl₂, pH 9.3), incubating it in a humid chamber at 94° C. for 5 min to dissociate any partial hairpin structure, and then slowly cooling down to room temperature for reannealing.

SBS reaction on a Chip with Four Photocleavable Fluorescent Nucleotide Analogues One microliter of a solution consisting of dATP-PC-ROX (60 pmol), 2 U of Thermo Sequenase DNA polymerase, and 1× reaction buffer was spotted on the surface of the chip, where the self-primed DNA moiety was immobilized. The nucleotide analogue was allowed to incorporate into the primer at 72° C. for 5 min. After washing with a mixture of SPSC buffer, 0.1% SDS, and 0.1% Tween 20 for 10 min, the surface was rinsed with dH₂O and ethanol successively, and then scanned with a ScanArray Express scanner to detect the fluorescence signal. To perform photocleavage, the glass chip was placed inside a chamber (50×50×50 mm) filled with acetonitrile/water (1/1, v/v) solution and irradiated for 1 min with the Nd-YAG laser at 355 nm. The light intensity applied on the glass surface was ca. 1.5 W/cm². After washing the surface with dH₂O and ethanol, the surface was scanned again to compare the intensity of fluorescence after photocleavage with the original fluorescence intensity. This process was followed by the incorporation of dGTP-PC-Bodipy-FL-510, with the subsequent washing, fluorescence detection, and photocleavage processes performed as described above. The same cycle was repeated 10 more times using each of the four photocleavable fluorescent nucleotide analogues complementary to the base on the template. For a negative control experiment, 1 µL solution containing dATP-PC-ROX (60 pmol), and 1× reaction buffer was added on to the DNA immobilized on the chip in the absence of DNA polymerase and then incubated at 72° C. for 5 min, followed by the same washing and detection steps as above.

REFERENCES

1. Collins, F. S., Green, E. D., Guttmacher, A. E. & Guyer, M. S. (2003) *Nature* 422, 835-847.
2. Thomas, J. W., Touchman, J. W., Blakesley, R. W., Bouffard, G. G., Beckstrom-Sternberg, S. M., Margulies, E. H., Blanchette, M., Siepel, A. C., Thomas, P. J. & McDowell, J. C. et al. (2003) *Nature* 424, 788-793.
3. Smith, L. M., Sanders, J. Z., Kaiser, R. J., Hughes, P., Dodd, C., Connell, C. R., Heiner, C., Kent, S. B. H. & Hood, L. E. (1987) *Nature* 321, 674-679.
4. Ju, J., Ruan, C., Fuller, C. W., Glazer, A. N. & Mathies, R. A. (1995) *Proc. Natl. Acad. Sci. USA* 92, 4347-4351.
5. Doherty, E. A. S., Kan, C. W. and Barron, A. E. (2003) *Electrophoresis,* 24, 4170-4180.
6. Drmanac, S., Kita, D., Labat, I., Hauser, B., Schmidt, C., Burczak, J. D. & Drmanac, R. (1998) *Nat. Biotechnol.* 16, 54-58.
7. Fu, D. J., Tang, K., Braun, A., Reuter, D., Darnhofer-Demar, B., Little, D. P., O'Donnell, M. J., Cantor, C. R. & Koster, H. (1998) *Nat. Biotechnol.* 16, 381-384.
8. Roskey, M. T., Juhasz, P., Smirnov, I. P., Takach, E. J., Martin, S. A. & Haff, L. A. (1996) *Proc. Natl. Acad. Sci. USA* 93, 4724-4729.
9. Edwards, J. R., Itagaki, Y. & Ju, J. (2001) *Nucleic Acids Res.* 29, e104 (p1-6).
10. Kasianowicz, J. J., Brandin, E., Branton, D. & Deamer, D. W. (1996) *Proc. Natl. Acad. Sci. USA* 93, 13770-13773.
11. Ronaghi, M., Uhlen, M. & Nyren, P. (1998) *Science* 281, 363-365.
12. Braslavsky, I., Hebert, B., Kartalov, E. & Quake, S. R. (2003) *Proc. Natl. Acad. Sci. USA* 100, 3960-3964.
13. Mitra, R. D., Shendure, J., Olejnik, J., Olejnik, E. K. & Church, G. M. (2003) *Anal. Biochem.* 320, 55-65.
14. Hyman, E. D. (1988) *Anal. Biochem.* 174, 423-436.
15. Ju, J., Li, Z., Edwards, J. & Itagaki, Y. (2003) U. S. Pat. No. 6,664,079.
16. Seo, T. S., Bai, X., Ruparel, H., Li, Z., Turro, N. J. & Ju, J. (2004) *Proc. Natl. Acad. Sci. USA,* 101, 5488-5493.
17. Rosenblum, B. B., Lee, L. G., Spurgeon, S. L., Khan, S. H., Menchen, S. M., Heiner, C. R. & Chen, S. M. (1997) *Nucleic Acids Res.* 25, 4500-4504.
18. Zhu, Z., Chao, J., Yu, H. & Waggoner, A. S. (1994) *Nucleic Acids Res.* 22, 3418-3422
19. Rajasekharan Pillai, V. N. (1980) Synthesis 1, 1-26. 20. Barany, F. (1991) *Proc. Natl. Acad. Sci. USA* 88, 189-193.
21. Antao, V. P., Lai, S. Y. & Tinoco, I. Jr. (1991) *Nucleic Acids Res.* 19, 5901-5905.

What is claimed is:

1. A method for determining the sequence of a DNA, wherein (i) 1000 or fewer copies of the DNA are bound to a solid substrate via 1,3-dipolar azide-alkyne cycloaddition chemistry and (ii) each copy of the DNA is a denatured single-stranded template and comprises a 5'-phosphorylated self-priming moiety covalently linked to a 3'-end of the DNA, comprising performing the following steps:

(a) contacting the bound DNA with a DNA polymerase and four photocleavable fluorescent nucleotide analogues under conditions permitting the DNA polymerase to catalyze DNA synthesis, wherein (i) the nucleotide analogues consist of an analogue of G, an analogue of C, an analogue of T and an analogue of A, so that a nucleotide analogue complementary to the residue of the single-stranded template being sequenced is incorporated into the DNA extension product on the 5'-phosphorylated self-priming moiety of the bound DNA by the DNA polymerase, and (ii) each of the four analogues has a pre-determined fluorescence emission wavelength which is different than the fluorescence emission wavelengths of the other three analogues;

(b) removing the unincorporated nucleotide analogues not incorporated into the DNA extension product on the 5'-phosphorylated self-priming moiety of the bound DNA;

(c) determining the identity of the incorporated nucleotide analogue and;

(d) repeating steps (a) to (c) for incorporation of the next nucleotide analogue complementary to the subsequent base of the bound single stranded template DNA, thereby determining the sequence of the DNA.

2. The method of claim 1, further comprising the step of photocleaving the fluorescent moiety from the incorporated nucleotide analogue following step (c).

3. The method of claim 1, wherein the solid substrate is glass or quartz.

4. The method of claim 1, wherein fewer than 100 copies of the DNA are bound to the solid substrate.

5. The method of claim 1, wherein fewer than 20 copies of the DNA are bound to the solid substrate.

6. The method of claim 1, wherein fewer than five copies of the DNA are bound to the solid substrate.

7. The method of claim 1, wherein one copy of the DNA is bound to the solid substrate.

8. A method for determining the sequence of an RNA, wherein (i) 1000 or fewer copies of the RNA are bound to a solid substrate via 1,3-dipolar azide-alkyne cycloaddition chemistry and (ii) each copy of the RNA is a single-stranded template and comprises a 5'-phosphorylated self-priming moiety covalently linked to a 3'-end of the bound RNA, comprising performing the following steps:

(a) contacting the bound RNA with a RNA polymerase and four photocleavable fluorescent nucleotide analogues under conditions permitting the RNA polymerase to catalyze RNA synthesis, wherein (i) the nucleotide analogues consist of an analogue of G, an analogue of C, an analogue of U and an analogue of A, so that a nucleotide analogue complementary to the residue of the single-stranded template being sequenced is incorporated into the RNA extension product on the 5'-phosphorylated self-priming moiety of the bound RNA by the RNA polymerase, and (ii) each of the four analogues has a pre-determined fluorescence emission wavelength which is different than the fluorescence emission wavelengths of the other three analogues;

(b) removing the unincorporated nucleotide analogues not incorporated into the RNA extension product on the 5' phosphorylated self-priming moiety of the bound RNA;

(c) determining the identity of the incorporated nucleotide analogue and;

(d) repeating steps (a) to (c) for incorporation of the next nucleotide analogue complementary to the subsequent base of the bound single stranded template RNA, thereby determining the sequence of the RNA.

9. The method of claim 8, further comprising the step of photocleaving the fluorescent moiety from the incorporated nucleotide analogue following step (c).

10. The method of claim 8, wherein the solid substrate is glass or quartz.

11. The method of claim 8, wherein fewer than 100 copies of the RNA are bound to the solid substrate.

12. The method of claim 8, wherein fewer than 20 copies of the RNA are bound to the solid substrate.

13. The method of claim 8, wherein fewer than five copies of the RNA are bound to the solid substrate.

14. The method of claim 8, wherein one copy of the RNA is bound to the solid substrate.

15. A composition of matter comprising a solid substrate having a DNA or an RNA bound thereto via 1,3-dipolar azide-alkyne cycloaddition chemistry, wherein (i) about 1000 or fewer copies of the DNA or the RNA are bound to the solid substrate, and (ii) each copy of the DNA or the RNA comprises a self-priming moiety.

16. A compound having the structure:
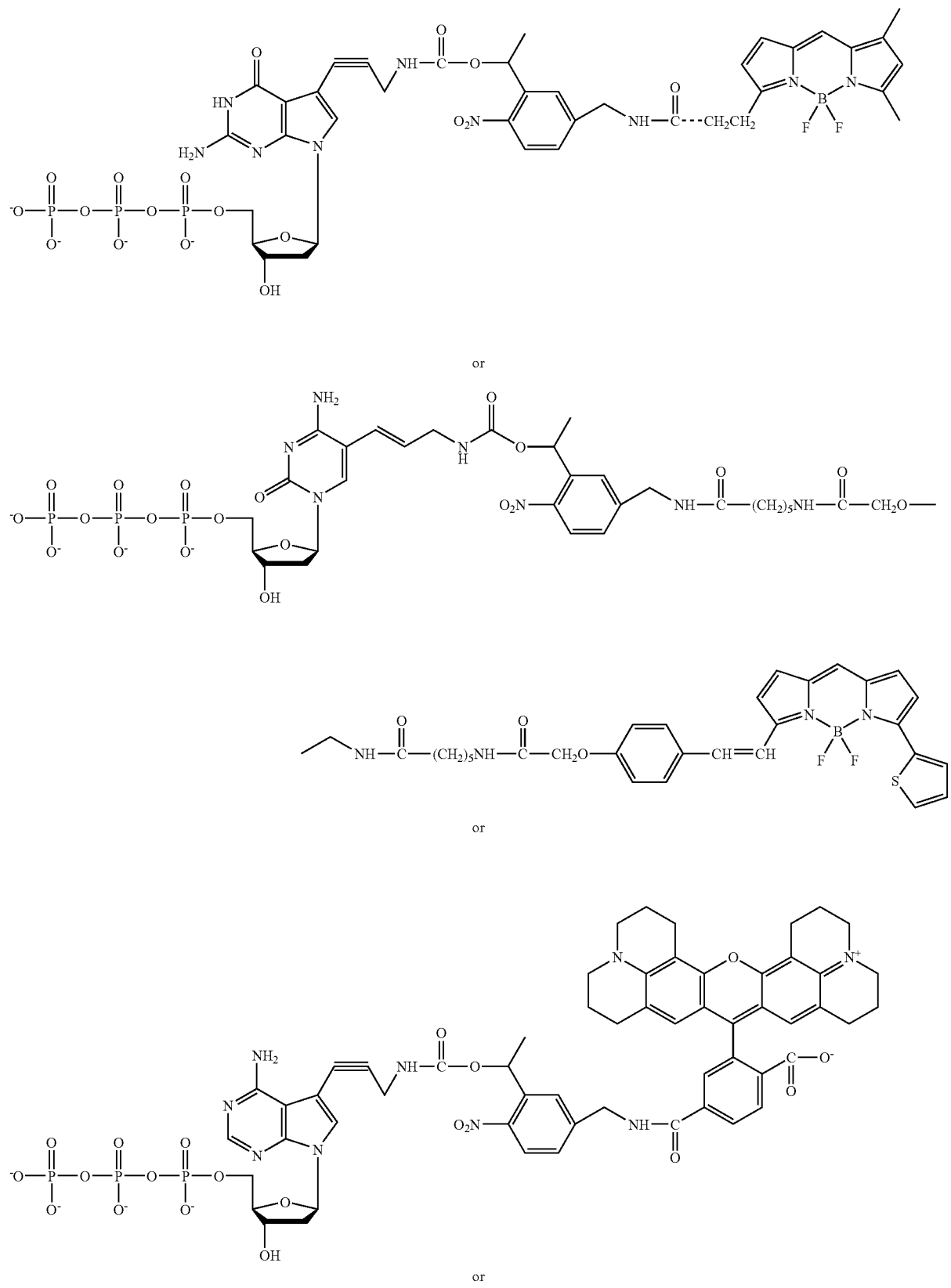
or

-continued

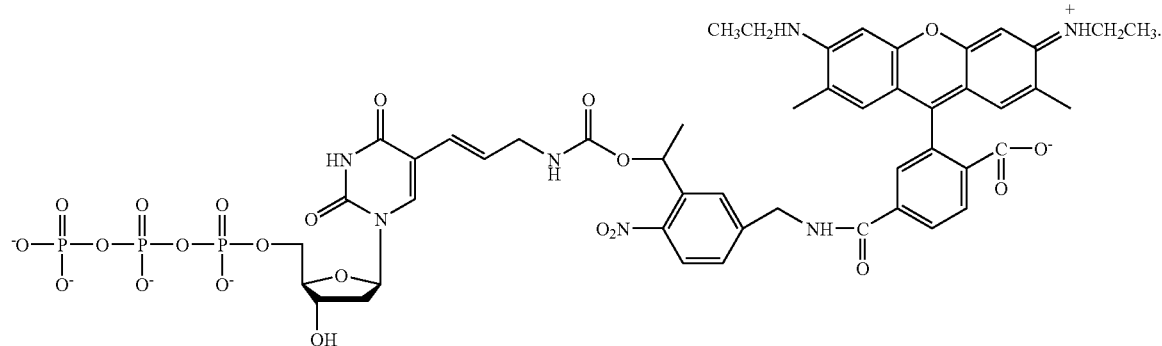

17. The compound of claim 16 having the having the structure:

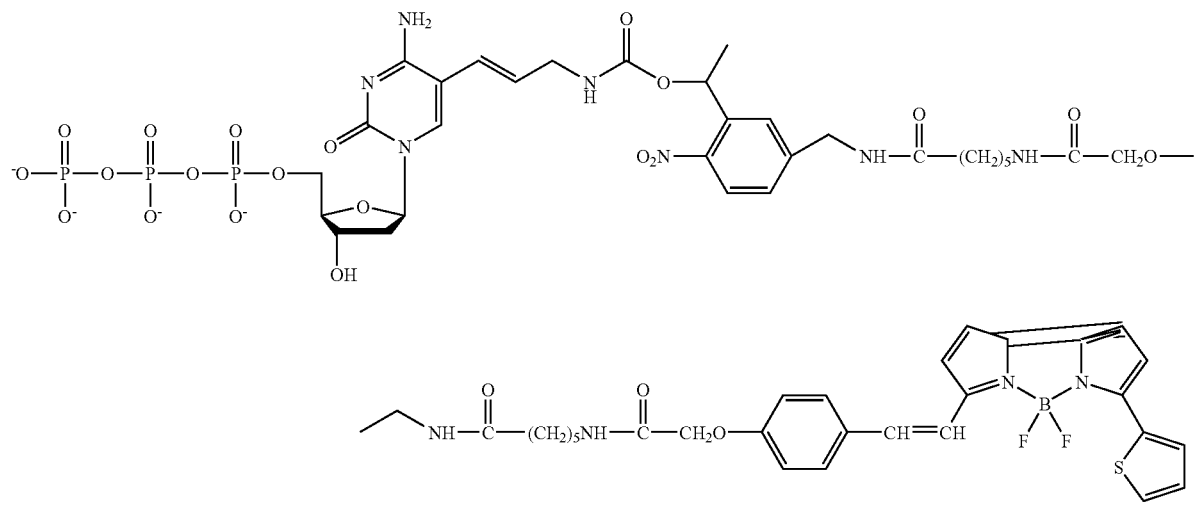

18. A composition of matter comprising a solid substrate having a RNA bound thereto via 1,3-dipolar azide-alkyne cycloaddition chemistry, wherein (i) about 1000 or fewer copies of the RNA are bound to the solid substrate, and (ii) each copy of the RNA comprises a self-priming moiety.

19. The compound of claim 16 having the structure:

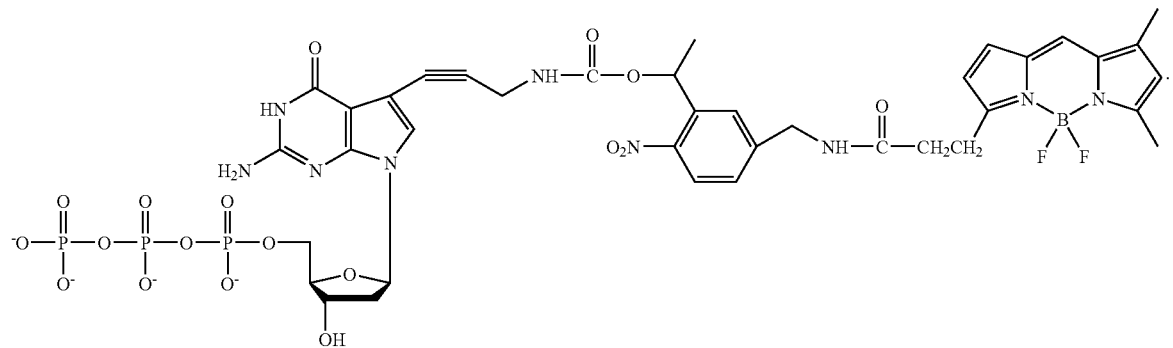

20. The compound of claim 16 having the structure:
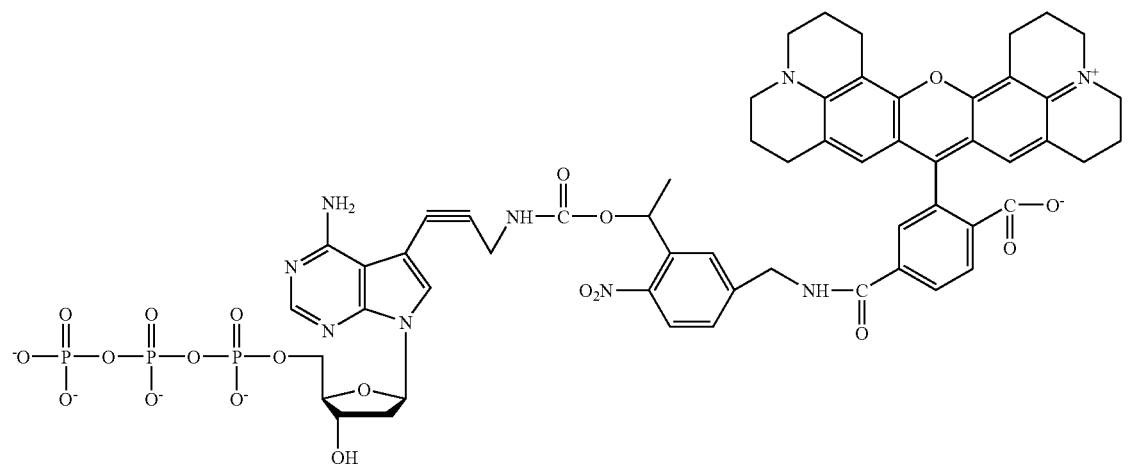
21. The compound of claim 16 having the structure:
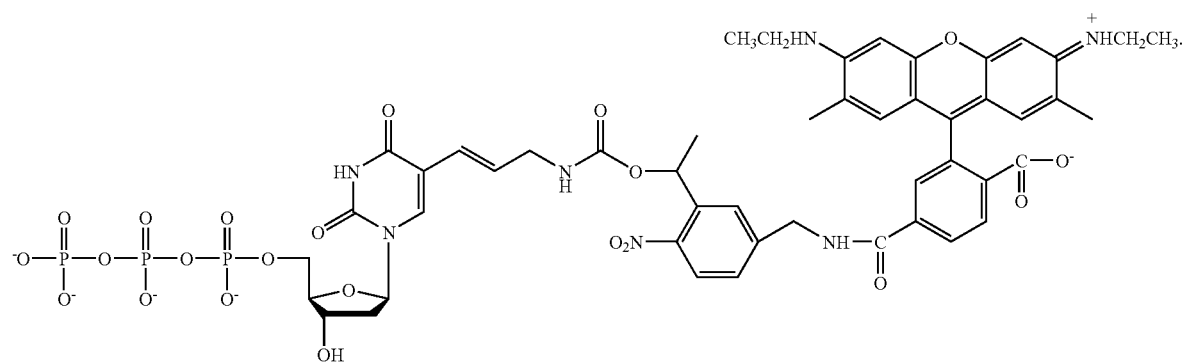
* * * * *

SEQUENCE LISTING

```
<160> NUMBER OF SEQ ID NOS: 10

<210> SEQ ID NO 1
<211> LENGTH: 18
<212> TYPE: DNA
<213> ORGANISM: ARTIFICIAL SEQUENCE
<220> FEATURE:
<223> OTHER INFORMATION: DNA/RNA HYBRID FOR SEQUENCING, BASED ON HUMAN
      P53

<400> SEQUENCE: 1
cagagccaac ctaggaga                                                    18

<210> SEQ ID NO 2
<211> LENGTH: 19
<212> TYPE: DNA
<213> ORGANISM: ARTIFICIAL SEQUENCE
<220> FEATURE:
<223> OTHER INFORMATION: HYBRID FOR TEST SEQUENCING BASED ON HUMAN P53

<400> SEQUENCE: 2
ucagagccaa cctaggaga                                                   19

<210> SEQ ID NO 3
<211> LENGTH: 20
<212> TYPE: DNA
<213> ORGANISM: ARTIFICIAL SEQUENCE
<220> FEATURE:
<223> OTHER INFORMATION: HYBRID FOR TEST SEQUENCING BASED ON HUMAN P53

<400> SEQUENCE: 3
gucagagcca acctaggaga                                                  20
```

```
<210> SEQ ID NO 4
<211> LENGTH: 21
<212> TYPE: DNA
<213> ORGANISM: ARTIFICIAL SEQUENCE
<220> FEATURE:
<223> OTHER INFORMATION: HYRBID FOR TEST SEQUENCING BASED ON HUMAN P53

<400> SEQUENCE: 4
agucagagcc aaccuaggag a                                         21

<210> SEQ ID NO 5
<211> LENGTH: 18
<212> TYPE: DNA
<213> ORGANISM: ARTIFICIAL SEQUENCE
<220> FEATURE:
<223> OTHER INFORMATION: PRIMER DIRECTED TO HUMAN P53 EXON 7

<400> SEQUENCE: 5
agaggatcca accgagac                                             18

<210> SEQ ID NO 6
<211> LENGTH: 60
<212> TYPE: DNA
<213> ORGANISM: ARTIFICIAL SEQUENCE
<220> FEATURE:
<223> OTHER INFORMATION: TEST DNA TEMPLATE BASED ON HUMAN P53 EXON 7

<400> SEQUENCE: 6
gtgtacatca acatcaccta ccaccatgtc agtctcggtt ggatcctcta ttgtgtccgg    60

<210> SEQ ID NO 7
<211> LENGTH: 100
<212> TYPE: DNA
<213> ORGANISM: ARTIFICIAL SEQUENCE
<220> FEATURE:
<223> OTHER INFORMATION: TEST DNA TEMPLATE BASED ON HUMAN P53

<400> SEQUENCE: 7
agcgactgct atcatgtcat atcgacgtgc tcactagctc tacatatgcg tgcgtgatca    60
gatgacgtat cgatgctgac tatagtctcc catgcgagtg                        100

<210> SEQ ID NO 8
<211> LENGTH: 24
<212> TYPE: DNA
<213> ORGANISM: ARTIFICIAL SEQUENCE
<220> FEATURE:
<223> OTHER INFORMATION: PRIMER BASED ON HUMAN P53

<400> SEQUENCE: 8
agcgactgct atcatgtcat atcg                                      24

<210> SEQ ID NO 9
<211> LENGTH: 24
<212> TYPE: DNA
<213> ORGANISM: ARTIFICIAL SEQUENCE
<220> FEATURE:
<223> OTHER INFORMATION: REVERSE PRIMER BASED ON HUMAN P53

<400> SEQUENCE: 9
cactcgcatg ggagactata gtca                                      24

<210> SEQ ID NO 10
```

```
<211> LENGTH: 40
<212> TYPE: DNA
<213> ORGANISM: ARTIFICIAL SEQUENCE
<220> FEATURE:
<223> OTHER INFORMATION: ARTIFICIAL LOOP PRIMER

<400> SEQUENCE: 10
gctgaattcc gcgttcgcgg aattcagcca ctcgcatggg                              40
```